US008691808B2

(12) United States Patent
Wang et al.

(10) Patent No.: US 8,691,808 B2
(45) Date of Patent: Apr. 8, 2014

(54) ANTIVIRAL COMPOUNDS AND THEIR METHODS OF USE

(75) Inventors: Jizhou Wang, Eagleville, PA (US); Xiaodong Fan, Center Valley, PA (US); Lidia Cristian, Princeton Junction, NJ (US)

(73) Assignee: Influmedix, Inc., Radnor, PA (US)

( * ) Notice: Subject to any disclaimer, the term of this patent is extended or adjusted under 35 U.S.C. 154(b) by 62 days.

(21) Appl. No.: 13/474,746

(22) Filed: May 18, 2012

(65) Prior Publication Data

US 2012/0295886 A1      Nov. 22, 2012

Related U.S. Application Data

(60) Provisional application No. 61/488,623, filed on May 20, 2011.

(51) Int. Cl.
| | | |
|---|---|---|
| C07D 223/14 | (2006.01) |
| C07D 313/10 | (2006.01) |
| A61K 31/335 | (2006.01) |
| A61K 31/55 | (2006.01) |
| A61P 31/16 | (2006.01) |

(52) U.S. Cl.
USPC ...... 514/212.04; 514/216; 514/450; 540/520; 540/581; 549/268

(58) Field of Classification Search
USPC ............. 514/212.04, 216, 450; 540/520, 581; 549/268
See application file for complete search history.

(56) References Cited

U.S. PATENT DOCUMENTS

| | | |
|---|---|---|
| 3,397,233 A | 8/1968 | Cairns |
| 5,846,514 A | 12/1998 | Foster et al. |
| 6,334,997 B1 | 1/2002 | Foster et al. |
| 2006/0270742 A1 | 11/2006 | Staunton et al. |
| 2011/0028510 A1 | 2/2011 | Altmeyer et al. |
| 2011/0201655 A1 | 8/2011 | Umeda et al. |

FOREIGN PATENT DOCUMENTS

WO      WO2011022191 A1      2/2011

OTHER PUBLICATIONS

Yurchenko et al. Organic Mass Spectrometry (1970), 3(11), 1401-1410.*
Bright et al., Incidence of adamantane resistance among influenza A (H3N2) viruses isolated worldwide from 1994 to 2005:a cause for concern; Lancet, 2005, 366, 1175-1181.
Chang et al., Membrane Permeabilization by Small Hydrophobic Nonstructural Proteins of Japanese Encephalitis Virus; J. Virol, 1999, 73(8): 6257.
Gonzalez et al., Viroporins, FEBS Lett., 2003, 552, 28-34.
Han et al., The NS3 Protein of Bluetongue Virus Exhibits Viroporin-like Properties, J. Biol. Chem., 2004, 279, 41, 43092-43097.
Han et al., Biochemical and Functional Characterization of the Ebola Virus VP24 Protein: Implications for a Role in Virus Assembly and Budding, J. Virology, 2003, 77(3), 1793-1800.
Ito et al., Evolutionary analysis of the influenza A virus M gene with comparison of the M1 and M2 proteins, J. Virol., 1991, 65, 5491-8.
Jefferson et al., Antivirals for influenza in healthy adults: systematic review, Lancet, 2006, 367, 303-13.
Khan et al., Biological and Chemical Terrorism:Strategic Plan for Preparedness and Response, Recommendations of the CDC Strategic Planning Workgroup, MMWR, 2000, 49, RR-4, 1-14.
Kiso et al., Resistant influenza A viruses in children treated with oseltamivir: descriptive study, Lancet, 2004, 364, 759-65.
Lamb et al., The proton selective ion channels of influenza A and B viruses, in Influenza Virology: Current Topics, Yoshihiro Kawaoka, ed., Chap 3, pp. 65-93, Caister Academic Press, Norfolk, England, Mar. 2006.
Scholtissek, et al., How to overcome resistance of influenza A viruses against adamantane derivatives, Antiviral Research, 1998, 37, 83-95.
Schulz et al., SSM-based electrophysiology, Methods, 2008, 46, 97-103.
Van Niekerk et al, Membrane Association of African Horsesickness Virus Nonstructural Protein NS3 Determines Its Cytotoxicity, Virology, 2001, 279, 499-508.
Wang et al, Exploring the Requirements for the Hydrophobic Scaffold and Polar Amine in Inhibitors of M2 from Influenza A Virus, ACS Med. Chem. Lett, 2011, 2, 307-312.

* cited by examiner

*Primary Examiner* — Bruck Kifle
(74) *Attorney, Agent, or Firm* — David W. Ladner; Ladner Patent Management LLC

(57) ABSTRACT

The present disclosure provides compounds having affinity for the M2 proton channel, useful for the treatment of viral infections such as influenza, which are of the Formula (I):

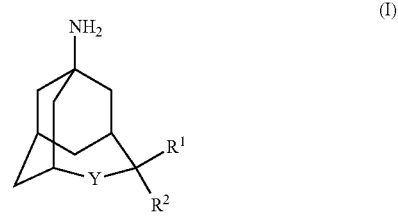

wherein $R^1$, $R^2$, and Y are as defined herein. Methods of preparing the compounds, pharmaceutical compositions containing the compounds, and methods of using the compounds in the treatment of viral infections such as influenza are also provided.

14 Claims, No Drawings

# ANTIVIRAL COMPOUNDS AND THEIR METHODS OF USE

RELATED APPLICATION

This patent application claims priority to U.S. Provisional Patent Application Ser. No. 61/488,623, filed May 20, 2011, the content of which is incorporated herein by reference in its entirety.

FIELD OF THE INVENTION

The present invention relates, in part, to methods of treatment, prevention, and inhibition of viral disorders. In one aspect, the present invention relates to inhibition of the M2 proton channel of influenza viruses (e.g., influenza A virus and/or influenza B virus) and other similar viroporins (e.g., VP24 of Ebola and Marburg viruses; and NS3 protein of Bluetongue). The present invention further relates to compounds which have been shown to possess antiviral activity, in particular, inhibiting the M2 proton channel (e.g., wild type and/or drug resistant influenza such as S31N influenza or other drug-resistant influenza strains) of influenza viruses and other similar viroporins.

BACKGROUND OF THE INVENTION

Viroporins are a growing class of membrane proteins that are important for viral replication and packaging. These proteins also affect cellular functions, including the cell vesicle system, glycoprotein trafficking and membrane permeability (Gonzalez et al., FEBS Lett., 2003, 552, 28-34). The M2 proton channel is a prototype for this class of proteins that is essential to the survival of the virus (Lamb et al., Wimmer E, editor, Receptor-Mediated Virus Entry into Cells, Cold Spring Harbor, N.Y., Cold Spring Harbor Press, 1994, p. 303-321).

Viroporins are essential components of a variety of viruses including Ebola, Marburg, Bluetongue, African horse sickness, foot and mouth disease, and Japanese encephalitis viruses. In particular, Ebola and Marburg viruses pose a particularly serious threat to human health and are classified as category A biowarfare agents by the Center for Disease Control (CDC) (Khan et al., MMWR, 2000, 49, RR-4, 1-14. VP24 from Ebola and Marburg viruses is an integral membrane protein that possesses viroporin activity similar to the M2 protein (Han et al., J. Virology, 2003, 77(3), 793-800). NS3 protein of Bluetongue is a viroporin that is critical for virus release (Han et al., J. Biol. Chem., 2004, 279, 41, 43092-43097). In addition, picronaviruses (Gonzalez et al., FEBS Lett., 2003, 552, 28-34), African horse sickness, and Japanese encephalitis encode proteins with viroporin activity that play central roles in viral pathogenesis (Van Niekerk et al., Virology, 2001, 279, 499-508; Chang et al., J. Virol., 1999, 73(8), 6257-6264).

Influenza viruses infect the upper and lower respiratory tracts and cause substantial morbidity and mortality annually. Influenza A viruses, which also infect a wide number of avian and mammalian species, pose a considerable public health burden with epidemic and pandemic potential. Influenza together with complications of the virus is consistently among the top 10 common causes of death, ranking higher than some other much more widely publicized killers, such as the HIV virus that causes AIDS. It is estimated that in annual influenza epidemics, About 5-15% of the world's population contracts influenza, resulting in an estimated 3-5 million cases of severe illness and 250,000 to 500,000 deaths around the world from influenza-associated complications. In the U.S., 10%-20% of the population is infected with the flu every year, with an average 0.1% mortality. The flu causes 36,000 deaths each year in the U.S., and 114,000 hospitalizations. The cost of influenza epidemics to the U.S. economy is estimated at $3-15 billion. Approximately 20% to 40% of the world's population became ill during the catastrophic "Spanish" flu pandemic in 1918, which killed an estimated 40 to 50 million people worldwide and 675,000 people in the United States. The "Asian" flu pandemic of 1957 resulted in the deaths of approximately 69,800 people in the United States and 2.0 to 7.4 million worldwide. The H1N1 swine flu pandemic in 2009 has caused about 3,000 deaths worldwide to date.

Tamiflu® (oseltamivir), which targets neuraminidase protein, is the only remaining orally administered anti-flu drug on the market and resistance to the drug is increasing with oseltamivir-resistant viruses arising during clinical use of the drug in children (Kiso et al., Lancet, 2004, 364, 759-65). Oseltamivir has been used for treatment of infected individuals and although it is FDA-approved for prophylaxis its usefulness for prophylactic treatment has been questioned in a recent systematic analysis of data from 51 controlled trials (Jefferson et al., Lancet, 2006, 367, 303-13). Thus, there is an immediate need to develop additional agents that inhibit the M2 proton channel and its drug-resistant forms, and in particular the most prevalent mutant form, S31N, but also in others including L26, V27, A30, and G34.

Influenza A and B viruses each encode a small oligomeric integral membrane protein, M2 of influenza A virus and BM2 of influenza B virus, each of which is a proton-selective ion channel. The M2 protein plays an important role during the early and late stages of the viral life cycle. Early in the cycle, the virus enters cells by receptor-mediated endocytosis, which places the virus into endosomal vesicles. Proton-pumping ATP-ases in the endosomal membrane lower the internal pH, which triggers the fusion of the viral envelope with the endosomal membrane and the release of the viral RNA into the cytoplasm. However, unless the inside of the virus is acidified prior to fusion, the RNA remains encapsulated by a matrix protein known as M1 (Ito et al., J. Virol., 1981, 65, 5491-8). The M2 protein provides a conduit for passage of protons into the interior of the virus, thereby promoting the dissociation of RNA from its matrix protein. This is a crucial step in uncoating of the virus and exposing its content to the cytoplasm of the host cell. In some strains of influenza A virus, the M2 protein is also important for equilibrating the pH of the lumen of the Golgi apparatus with the cytoplasm, thus preventing a premature conformational change in the viral hemagglutinin at the wrong time and in the wrong place (Ciampor et al., Acta Virologica, 1995, 39, 171-181) Inhibition of M2 at this later stage of the viral life cycle prevents viral maturation and release from the host cell.

Several features make M2 an excellent target for an anti-influenza drug. It is essential and present in all known isolates of influenza A virus, and it is already validated as a drug target. Although a variety of mutations occur naturally and can be isolated in cell culture, one mutant in particular, S31N, predominates in more than 98% of the transmissible resistant viral strains isolated from patients in the last decade (Bright et al., Lancet, 2005, 366, 1175-1181).

Thus, there is a great need for additional compositions and methods of treatment based on the use of antiviral compounds against key viral pathogens and, optionally, less prone to the development of resistance by those pathogens. Moreover, there is a great need for additional compositions and methods of treatment based on the use of antiviral compounds that are effective in the treatment of viral pathogens that have already developed resistance to existing antiviral agents. In particular, there is a great need for effective compositions and methods for the treatment of viral infections such as influenza, Ebola, Marburg, bluetongue, foot and mouth disease, African horse sickness, and Japanese encephalitis (including the strains that have already developed resistance to existing antiviral agents). The present invention is directed to these and other important ends.

SUMMARY OF THE INVENTION

The present invention is directed to compounds of Formula I:

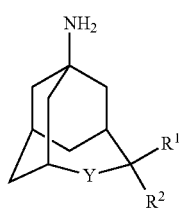

(I)

wherein
Y is selected from $CR^1R^2$, $NR^3$, and O;
$R^1$ and $R^2$ are each independently selected from
  H, halo (F, Cl, Br, I), cyano, $OR^7$, $C(O)R^{10}$, $C(O)_2R^{10}$, $C(O)NR^8R^9$, $C_1$-$C_6$ alkyl, and $C_1$-$C_6$ halogenated alkyl; or
$R^1$ and $R^2$ together form a double bond functional group selected from oxo (=O), and oximino (=N—$OR^7$);
$R^3$ is selected from
  H, $C_1$-$C_6$ alkyl, and $C_3$-$C_6$ alkenyl;
$R^7$ is selected from
  H, $C_1$-$C_6$ alkyl, $C_1$-$C_6$ halogenated alkyl, $C_3$-$C_6$ alkenyl, $C_3$-$C_6$ alkynyl, $C_3$-$C_8$ cycloalkyl, $C_5$-$C_8$ cycloalkenyl, $C(O)R^{10}$, $C(O)NR^{12}R^{12}$, $C_1$-$C_5$ heterocyclyl, aryl, arylalkyl, heteroaryl, and heteroarylalkyl;
$R^8$ and $R^9$ are each independently selected from
  H, $C_1$-$C_6$ alkyl, $C_3$-$C_6$ alkenyl, $C_3$-$C_6$ alkynyl, $C_3$-$C_8$ cycloalkyl, $C_5$-$C_8$ cycloalkenyl, $C(O)R^{10}$, $C(O)OR^{11}$, $C(O)NR^{12}R^{12}$, $S(O)_2R^{11}$, $S(O)_2NR^{12}R^{12}$, $C_1$-$C_5$ heterocyclyl, aryl, arylalkyl, heteroaryl, and heteroarylalkyl;
or
  $R^8$ and $R^9$ together with the nitrogen atom to which they are attached, form a 4-7-membered heterocyclic ring; which is unsubstituted or substituted one or more times with $C_{1-4}$ alkyl, $C_{1-4}$ halogenated alkyl, $C_{1-4}$ alkoxy, oxo, or any combination thereof;
$R^{10}$ is selected from
  H, $C_1$-$C_6$ alkyl, $C_1$-$C_6$ halogenated alkyl, $C_3$-$C_6$ alkenyl, $C_3$-$C_6$ alkynyl, $C_3$-$C_8$ cycloalkyl, $C_5$-$C_8$ cycloalkenyl, $C_1$-$C_5$ heterocyclyl, aryl, arylalkyl, heteroaryl, and heteroarylalkyl;
$R^{11}$ is selected from
  $C_1$-$C_6$ alkyl, $C_1$-$C_6$ halogenated alkyl, $C_3$-$C_6$ alkenyl, $C_3$-$C_6$ alkynyl, $C_3$-$C_8$ cycloalkyl, $C_5$-$C_8$ cycloalkenyl, $C_1$-$C_5$ heterocyclyl, aryl, arylalkyl, heteroaryl, and heteroarylalkyl;
$R^{12}$ is independently selected from:
  H, $C_1$-$C_6$ alkyl, $C_3$-$C_6$ alkenyl, $C_3$-$C_6$ alkynyl, $C_3$-$C_8$ cycloalkyl, $C_5$-$C_8$ cycloalkenyl, $C_1$-$C_5$ heterocyclyl, aryl, arylalkyl, heteroaryl, and heteroarylalkyl; or two $R^{12}$ residues together with the nitrogen atom to which they are attached, form a 4-7-membered heterocyclic ring; which is unsubstituted or substituted one or more times with $C_{1-4}$-alkyl, $C_{1-4}$ halogenated alkyl, $C_{1-4}$-alkoxy, oxo, or any combination thereof;

and pharmaceutically acceptable salts or solvates (e.g., hydrates) thereof.

According to one embodiment of the present invention there is provided a compound of Formula (I) wherein Y is O, and $R^1$ and $R^2$ are as described above.

According to a second embodiment of the present invention there is provided a compound of Formula (I) wherein Y is O, and $R^1$ and $R^2$ are both H.

According to a third embodiment of the present invention there is provided a compound of Formula (I) wherein Y is O, and $R^1$ and $R^2$ together form an oxo (=O) group.

According to a fourth embodiment of the present invention there is provided a compound of Formula (I) wherein Y is $NR^3$, and $R^1$ and $R^2$ are as described above.

According to a fifth embodiment of the present invention there is provided a compound of Formula (I) wherein Y is $NR^3$, and $R^1$ and $R^2$ together form an oxo (=O) group.

According to a sixth embodiment of the present invention there is provided a compound of Formula (I) wherein Y is $NR^3$, and $R^1$ and $R^2$ are both H.

According to a seventh embodiment of the present invention there is provided a compound of Formula (I) wherein Y is $CR^1R^2$, and $R^1$ and $R^2$ are as described above.

According to a eighth embodiment of the present invention there is provided a compound of Formula (I) wherein Y is $CR^1R^2$, and $R^1$ and $R^2$ are as described above, provided that at least one of $R^1$ or $R^2$ must be other than H.

According to a ninth embodiment of the present invention there is provided a compound of Formula (I) wherein Y is $CR^1R^2$, and $R^1$ and $R^2$ are independently selected from hydrogen, halogen, alkyl, and $OR^7$; and $R^7$ is H.

According to a tenth embodiment of the present invention there is provided a compound of Formula (I) wherein Y is defined as $CR^1R^2$ wherein $R^1$ and $R^2$ together form a double bond functional group selected from oxo (=O), and oximino (=N—$OR^7$).

In accordance with the present invention there are also provided the following specific embodiments of the above compounds:

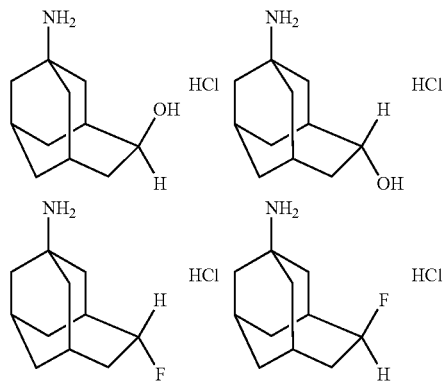

-continued

[Chemical structures of various aminotricyclo[4.3.1.1³,⁸]undecane HCl salts]

In accordance with the present invention there are provided the following specific embodiments of the above compounds:

exo-1-Aminotricyclo[4.3.1.1³,⁸]undecan-4-ol hydrochloride, endo-1-Aminotricyclo[4.3.1.1³,⁸]undecan-4-ol hydrochloride, endo-4-Fluorotricyclo[4.3.1.1³,⁸]undecan-1-amine hydrochloride, exo-4-Fluorotricyclo[4.3.1.1³,⁸]undecan-1-amine hydrochloride, 4-Fluorotricyclo[4.3.1.1³,⁸]undecan-1-amine hydrochloride, 4-Iodotricyclo[4.3.1.1³,⁸]undecan-1-amine hydrochloride, exo-1-Aminotricyclo[4.3.1.1³,⁸]undecane-4-carbonitrile hydrochloride, endo-1-Aminotricyclo[4.3.1.1³,⁸]undecane-4-carbonitrile hydrochloride, exo-4-(Difluoromethyl)tricyclo[4.3.1.1³,⁸]undecan-1-amine hydrochloride, endo-4-(Difluoromethyl)tricyclo[4.3.1.1³,⁸]undecan-1-amine hydrochloride, 1-Aminotricyclo[4.3.1.1³,⁸]undecan-4-one oxime hydrochloride, 1-Amino-4-oxatricyclo[4.3.1.1³,⁸]undecan-5-one hydrochloride, 1-Amino-4-azatricyclo[4.3.1.1³,⁸]undecan-5-one hydrochloride, 4-Azatricyclo[4.3.1.1³,⁸]undecan-1-amine dihydrochloride 4-Oxatricyclo[4.3.1.1³,⁸]undecan-1-amine hydrochloride, and pharmaceutically acceptable salts, free bases, or solvates (e.g., hydrates) thereof, or solvates of pharmaceutically acceptable salts thereof.

According to other embodiments of the present invention there is provided a method for treating a viral infection in a mammal, where the viral infection is influenza A virus, influenza B virus, or similar viroporins (e.g., VP24 of Ebola and Marburg viruses; and NS3 protein of Bluetongue). According to other embodiments of the present invention there is provided a pharmaceutical composition comprising a compound of Formula (I) in combination with a pharmaceutically acceptable carrier, diluent or excipient.

Definitions

As used herein, the term "halogen" refers to F, Cl, Br, and I. Preferred halogens are F and Cl.

As used herein, the term "alkyl" refers to a straight or branched saturated monovalent cyclic or acyclic hydrocarbon radical, having the number of carbon atoms as indicated (or where not indicated, an acyclic alkyl group preferably has 1-20, more preferably 1-6, more preferably 1-4 carbon atoms and a cyclic alkyl group preferably has 3-20, preferably 3-10, more preferably 3-7 carbon atoms), optionally substituted with one, two, three or more substituents independently selected from the group set out above. Suitable alkyl groups include, but are not limited to, the linear alkyl radicals methyl, ethyl, propyl, isopropyl, butyl, sec-butyl, tert-butyl, pentyl, hexyl, heptyl, octyl, nonyl, decyl, undecyl, and dodecyl. Other examples of suitable alkyl groups include, but are not limited to, the substituted linear alkyl radicals 1-, 2- or 3-methylbutyl, 1,1-, 1,2- or 2,2-dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

The alkyl groups include cycloalkyl groups, e.g., monocyclic, bicyclic or tricyclic saturated hydrocarbon radical having 3 to 8 carbon atoms, preferably 3 to 6 carbon atoms. Suitable cycloalkyl groups include, but are not limited to, cyclopropyl, cyclobutyl, cyclopentyl, cyclohexyl, cycloheptyl, cyclooctyl, and norbornyl. Other suitable cycloalkyl groups include, but are not limited to, spiropentyl, bicyclo [2.1.0]pentyl, bicyclo[3.1.0]hexyl, spiro[2.4]heptyl, spiro [2.5]octyl, bicyclo[5.1.0]octyl, spiro[2.6]nonyl, bicyclo [2.2.0]hexyl, spiro[3.3]heptyl, and bicyclo[4.2.0]octyl.

The alkyl groups also include cycloalkylalkyl in which the cycloalkyl portions have preferably 3 to 8 carbon atoms, preferably 4 to 6 carbon atoms and alkyl the portions have preferably 1 to 8 carbon atoms, preferably 1 to 4 carbon atoms. Suitable examples include, but are not limited to, cyclopentylethyl and cyclopropylmethyl.

Substituted alkyl, alkenyl, alkynyl, and cycloalkyl groups refer to the alkyl, alkenyl, alkynyl, and cycloalkyl groups above which are substituted one or more times by, for example, halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, phenyl, oxo, sulfo, and acyloxy (e.g., acetoxy).

In the cases where alkyl is a substituent (e.g., alkyl substituents on aryl and heteroaryl groups) or is part of a substituent (e.g., in the alkylamino, dialkylamino, hydroxyalkyl, hydroxyalkoxy, alkylthio, alkylsulphinyl, and alkylsulphonyl substituents), the alkyl portion preferably has 1 to 12 carbon atoms, especially 1 to 8 carbon atoms, in particular 1 to 4 carbon atoms.

As used herein, the term "alkenyl" refers to a straight or branched unsaturated monovalent acyclic or cyclic hydrocarbon radical having one or more C=C double bonds and having the number of carbon atoms as indicated (or where not indicated, an acyclic alkenyl group preferably has 2-20, more preferably 2-6, more preferably 2-4 carbon atoms and a cyclic alkenyl group preferably has 4-20, more preferably 4-6 carbon atoms), optionally substituted with one, two, three or more substituents independently selected from the group set out above. By way of non-limiting examples, suitable alkenyl groups include vinyl, propenyl, butenyl, pentenyl and hexenyl.

As used herein, the term "alkynyl" refers to a straight or branched unsaturated monovalent acyclic or cyclic hydrocarbon radical having one or more triple C/C bonds and having the number of carbon atoms as indicated (or where not indicated, an acyclic alkynyl group preferably has 2-20, more preferably 2-6, more preferably 2-4 carbon atoms and a cyclic alkynyl group preferably has 7-20, more preferably 8-20 carbon atoms), optionally substituted with one, two, three or more substituents independently selected from the group set out above.

Substituted alkyl, alkenyl, alkynyl, and cycloalkyl groups refer to the alkyl, alkenyl, alkynyl, and cycloalkyl groups above which are substituted one or more times by, for example, halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, phenyl, oxo, sulfo, and acyloxy (e.g., acetoxy).

As used herein, the term "alkoxy" or the term "alkyloxy" refers to the group alkyl-O—, where alkyl is as defined above and where the alkyl moiety may optionally be substituted by one, two, three or more substituents as set out above for alkyl. By way of non-limiting examples, suitable alkoxy groups include methoxy, ethoxy, n-propoxy, iso-propoxy, n-butoxy, tert-butoxy, sec-butoxy, n-pentoxy, n-hexoxy and 1,2-dimethylbutoxy. The term "cycloalkyloxy" refers to the group cyclicalkyl-O—, where cyclicalkyl is as defined above and where the cyclicalkyl moiety may be optionally substituted by one, two, three or more substituents as set out above for alkyl.

As used herein, the term "aryl" refers to an aromatic carbocyclic radical containing 6 to 14 carbon atoms, preferably 6 to 12 carbon atoms, especially 6 to 10 carbon atoms. Suitable aryl groups include, but are not limited to, phenyl, and naphthyl. Substituted aryl groups include the above-described aryl groups which are substituted one or more times by, for example, halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, phenyl, and acyloxy (e.g., acetoxy).

As used herein, the terms "arylalkyl", or equivalently ""aralkyl" refers to an aryl-alkyl-radical in which the aryl and alkyl portions are in accordance with the previous descriptions. Suitable examples include, but are not limited to, benzyl, 1-phenethyl, 2-phenethyl, phenpropyl, phenbutyl, phenpentyl, and naphthalenemethyl.

As used herein, the term "heteroaryl" refers to an unsaturated heterocyclic group having one or two rings and a total number of 5 to 10 ring atoms wherein at least one of the ring atoms is preferably an N, O or S atom. Preferably, the heteroaryl group contains 1 to 3, especially 1 or 2, hetero-ring atoms selected from N, O and S. Suitable heteroaryl groups include, for example, furyl, benzothienyl, benzofuranyl, pyrrolyl, pyrazolyl, imidazolyl, pyridyl, pyrimidinyl, isoxazolyl, quinolinyl, azaindolyl, naphthyridinyl, thiazolyl, and the like. Preferred heteroaryl groups include, but are not limited to, furyl, benzothienyl, benzofuranyl, pyrrolyl, pyrazolyl, imidazolyl, pyridyl, pyrimidinyl, isoxazolyl, and thiazolyl.

Substituted heteroaryl groups refer to the heteroaryl groups described above which are substituted in one or more places by preferably halogen, aryl, alkyl, alkoxy, cyano, halogenated alkyl (e.g., trifluoromethyl), nitro, oxo, amino, alkylamino, and dialkylamino.

As used herein, the term "hetereocyclyl" refers to a non-aromatic, saturated or partially unsaturated, cyclic group containing at least one hetero-ring atom, preferably selected from N, S, and O, for example, 1,2,3,4,-tetrahydroquinolyl, dihydrobenzofuranyl, dihydrobenzodioxepinyl, dihydrobenzodioxinyl, dihydroindolyl, benzodioxolyl, 3-tetrahydrofuranyl, piperidinyl, imidazolinyl, imidazolidinyl, pyrrolinyl, pyrrolidinyl, morpholinyl, piperazinyl, oxazolidinyl, and indolinyl.

As used herein, the term "heteroaralkyl" (heteroarylalkyl) refers to a heteroaryl-alkyl-group wherein the heteroaryl and alkyl portions are in accordance with the previous discussions. Suitable examples include, but are not limited to, pyridylmethyl, thienylmethyl, pyrimidinylmethyl, pyrazinylmethyl, isoquinolinyl-methyl, pyridylethyl and thienylethyl.

In the aralkyl (arylalkyl) groups and heteroaralkyl (heteroarylalkyl), and heteroalkyl groups, "alkyl" refers to a divalent alkylene group preferably having 1 to 4 carbon atoms.

Carbocyclic structures are non-aromatic monocyclic or bicyclic structures containing 5 to 14 carbon atoms, preferably 6 to 10 carbon atoms, wherein the ring structure(s) optionally contain at least one C=C bond.

As used herein, the term "acyl" refers to an alkanoyl radical having 2 to 4 carbon atoms. Suitable acyl groups include, but are not limited to, formyl, acetyl, propionyl, and butanoyl.

Substituted radicals preferably have 1 to 3 substituents, especially 1 or 2 substituents.

Compounds of the invention are exemplified by the following compounds listed below and depicted in Table 1:

The compounds of the present invention include, but are not limited to:

exo-1-aminotricyclo[4.3.1.1$^{3,8}$]undecan-4-ol hydrochloride, endo-1-aminotricyclo[4.3.1.1$^{3,8}$]undecan-4-ol hydrochloride, endo-4-fluorotricyclo[4.3.1.1$^{3,8}$]undecan-1-amine hydrochloride, exo-4-fluorotricyclo[4.3.1.1$^{3,8}$]undecan-1-amine hydrochloride, 4-fluorotricyclo[4.3.1.1$^{3,8}$]undecan-1-amine hydrochloride, 4-iodotricyclo[4.3.1.1$^{3,8}$]undecan-1-amine hydrochloride, exo-1-aminotricyclo[4.3.1.1$^{3,8}$]undecane-4-carbonitrile hydrochloride, endo-1-aminotricyclo[4.3.1.1$^{3,8}$]undecane-4-carbonitrile hydrochloride, exo-4-(difluoromethyl)tricyclo[4.3.1.1$^{3,8}$]undecan-1-amine hydrochloride, endo-4-(difluoromethyl)tricyclo[4.3.1.1$^{3,8}$]undecan-1-amine hydrochloride, 1-aminotricyclo[4.3.1.1$^{3,8}$]undecan-4-one oxime hydrochloride, 1-amino-4-oxatricyclo[4.3.1.1$^{3,8}$]undecan-5-one hydrochloride, 1-amino-4-azatricyclo[4.3.1.1³,⁸]undecan-5-one hydrochloride, 4-azatricyclo[4.3.1.1³,⁸]undecan-1-amine dihydrochloride 4-oxatricyclo[4.3.1.1³,⁸]undecan-1-amine hydrochloride, and pharmaceutically acceptable salts or solvates (e.g., hydrates) thereof, or solvates of pharmaceutically acceptable salts thereof.

TABLE 1

| Example No | Structure | LC/MS Data |
|---|---|---|
| 1 | | $[M+1]^+$ 182 at 0.87 min (Analytical Method A) |
| 2 | | $[M+1]^+$ 182 at 0.50 min (Analytical Method A) |
| 3 | | $[M+1]^+$ 184 at 1.03 min (Analytical Method A) |
| 4 | | $[M+1]^+$ 184 at 1.34 min (Analytical Method A) |
| 5 | | $[M+1]^+$ 292 at 1.71 min (Analytical Method A) |
| 8 | | $[M+1]^+$ 191.1 at 1.31 min (Analytical Method A) |
| 9 | 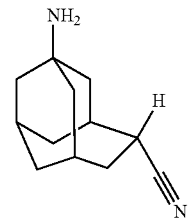 | $[M+1]^+$ 191.1 at 1.26 min (Analytical Method A) |
| 10 | 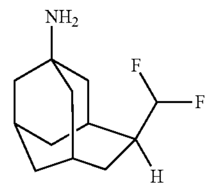 | $[M+1]^+$ 236 at 1.63 min (Analytical Method A) |
| 11 | 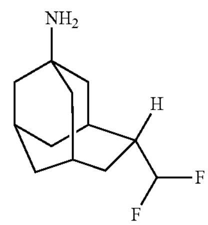 | $[M+1]^+$ 236 at 1.68 min (Analytical Method A) |
| 12 | 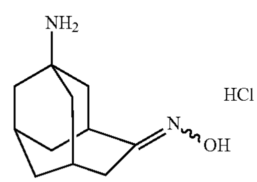 [SMILES: NC12CC3CC(=NO)C(CC(C3)C1)C2 ; Cl] | $[M+1]^+$ 195 at 0.90 min (Analytical Method A) |
| 13 | 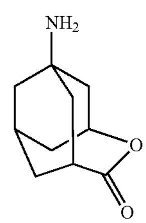 | $[M+1]^+$ 166 at 0.48 min (Analytical Method A) |
| 14 | 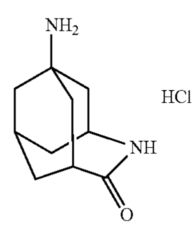 [SMILES: NC12CC3CC(C1)NC(=O)C(C3)C2 ; Cl] | $[M+1]^+$ 180 at 0.47 min (Analytical Method A) |
| 15 | 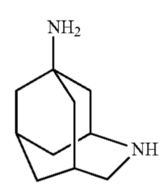 | $[M+1]^+$ 167 at 0.46 min (Analytical Method A) |

TABLE 1-continued

| Example No | Structure | LC/MS Data |
|---|---|---|
| 16 | (adamantane with NH$_2$, HCl, O) | [M + 1]$^+$ 168 at 0.84 min (Analytical Method A) |

Analytical HPLC/MS was performed on a 3 mm×50 mm Pursuit 3 Diphenyl column using a gradient of, typically, 5/95 to 100/0 acetonitrile (0.1% formic acid)/water (0.1% formic acid) over 7 min (Analytical Method A).

Additional aspects of the present invention include pharmaceutical compositions comprising a compound of this invention and a pharmaceutically acceptable carrier and, optionally, one or more additional active agent(s) as discussed below. Further aspects include methods of treating a disease state related to or modulated by the M2 channel, in a patient, such as a mammal, e.g., a human, e.g., those disease states mentioned herein.

Additionally, the present invention is directed to a pharmaceutical composition comprising a therapeutically effective amount of a compound of the present invention in combination with a therapeutically effective amount of one or more agents active against Influenza (A) or Influenza (B) viruses and other Viroporin-type viruses. Specific viral agents include Tamiflu®, Relenza®, and peramivir.

Even further, the present invention is directed to a method of treating a viral infection in a mammal comprising administering to a mammal in need thereof, a therapeutically effective amount of the compound of Formula (I) in combination with immunizations or vaccines that are effective in preventing or lessening the symptoms of influenza.

All methods comprise administering to the patient in need of such treatment an effective amount of one or more compounds of the invention.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of this invention can be prepared from readily available starting materials using the following general methods and procedures. It will be appreciated that where typical or suitable process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C NMR), infrared spectroscopy (IR), spectrophotometry (e.g., UV-visible), or mass spectrometry, or by chromatography such as high performance liquid chromatography (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in P. G. M. Wuts and T. Greene, *Greene's Protective Groups in Organic Synthesis*, 4th. Ed., Wiley & Sons, 2006, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of the invention can be prepared, for example, using the reaction pathways and techniques as described below.

As shown in Scheme 1, ketone 1-1 [PG$^1$ is an amine protecting group (such as tert-butyloxycarbonyl or Boc; or acetyl)] can be reacted with diazomethane (CH$_2$N$_2$) resulting in cycloalkanone ring expansion to afford ketone 1-2. Ketone 1-2 can be reduced to alcohol 1-3 by using a suitable such as metal borohydride (e.g. sodium borohydride). Alcohol 1-3 can be reacted with a halogenating reagent such as (diethylamino) sulfur trifluoride (DAST) or I$_2$/PPh$_3$ to afford the halogenated (fluorinated or iodinated) 1-4. The protecting group PG$_1$ of compound 1-4 can be removed under suitable conditions to afford compound 1-5. Dehalogenation of 1-4 (X=I) with Bu$_3$SnH/AIBN followed by deprotection produced 1-6. Those skilled in the art would readily choose suitable conditions depending on the protecting group PG$_1$ used, for example, acid conditions can be used to remove Boc.

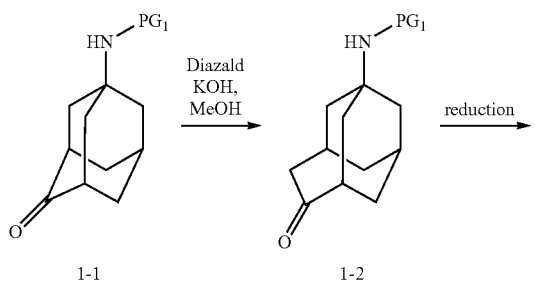

Scheme 1

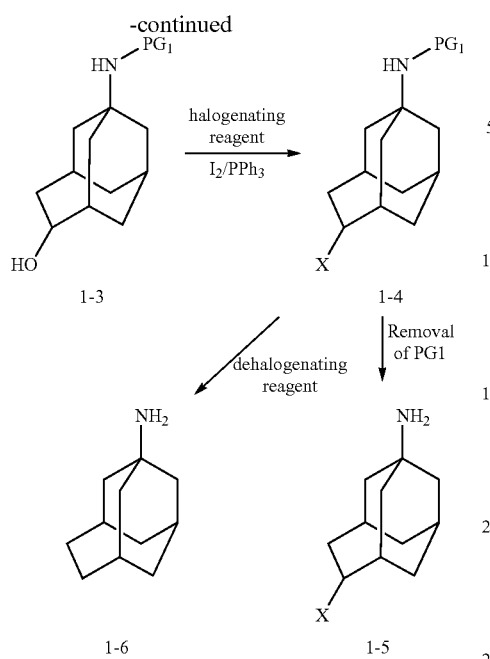

As shown in Scheme 2, ketone 1-2 ($PG_1$ is an amine protecting group (such as tert-butyloxycarbonyl or Boc; or acetyl)) can be reacted with TosMic/KOH resulting in nitrile 2-2. Nitrile 2-2 can be reduced to aldehyde 2-3 by using a suitable such as metal borohydride (e.g. DIBAL-H). Aldehyde 2-3 can be reacted with a halogenating reagent such as (diethylamino) sulfur trifluoride (DAST) to afford the halogenated (fluorinated) 2-4. The protecting group $PG_1$ of compound 2-4 can be removed under suitable conditions to afford compound 2-5.

As shown in Scheme 3, ketone 1-2 (PG is an amine protecting group (such as tert-butyloxycarbonyl or Boc; or acetyl)) can be reacted with hydroxylamine resulting in oxime 3-2. The protecting group of oxime 3-2 can be removed under suitable conditions to afford compounds 3-3.

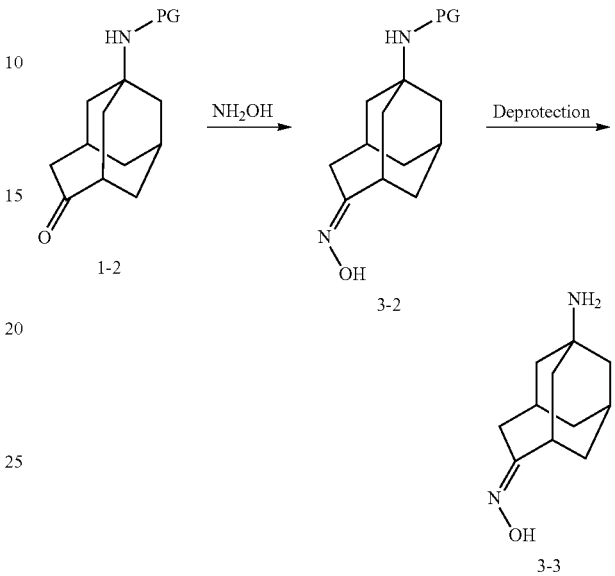

As shown in Scheme 4, ketone 1-1 (PG is an amine protecting group (such as tert-butyloxycarbonyl or Boc; or acetyl)) can be subjected to Bayer-Villager reaction conditions to provide ester 4-2. Lactone 4-2 can be reduced to ether 4-4 by using a suitable reducing agent such as triethylsilane and indium(III) bromide. The protecting group PG of com-

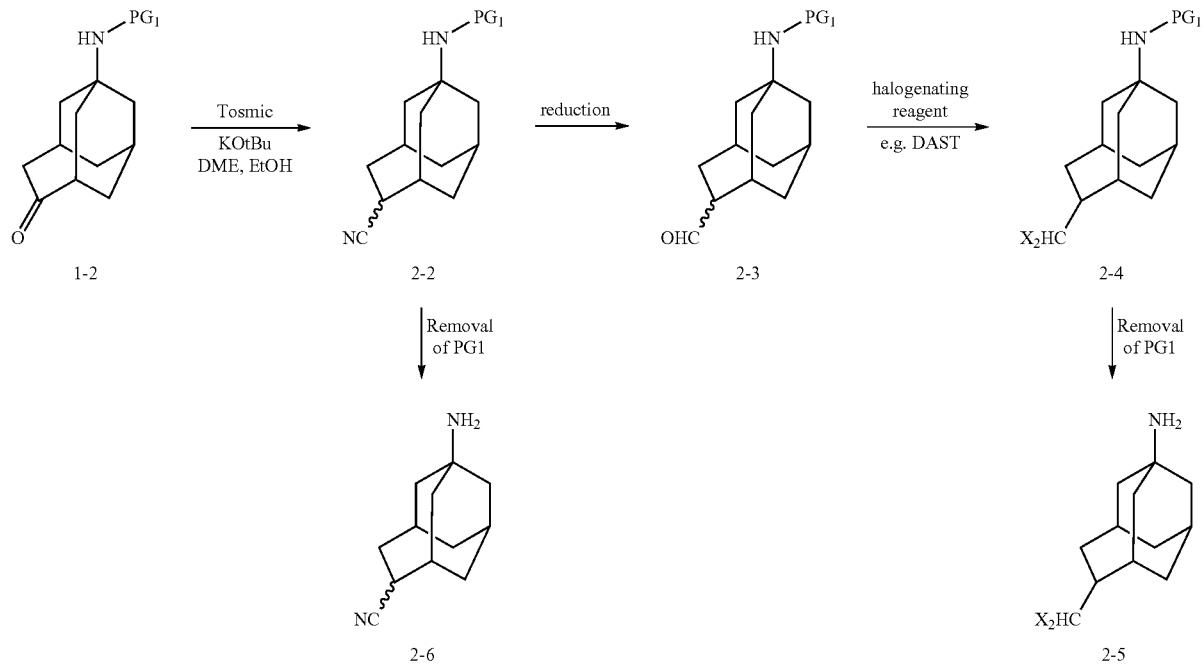

pounds 4-2 and 4-4 can be removed under suitable conditions to afford compounds 4-3 and 4-5.

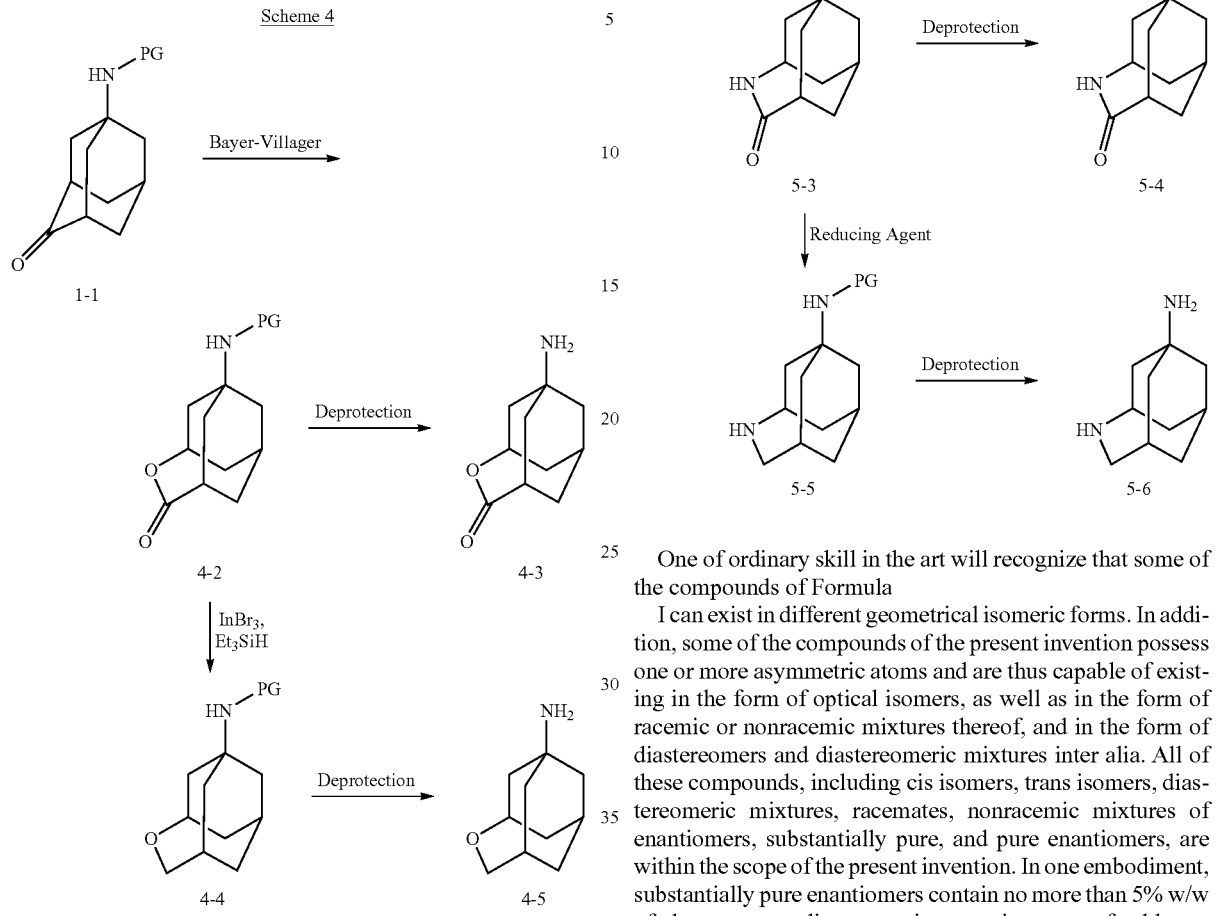

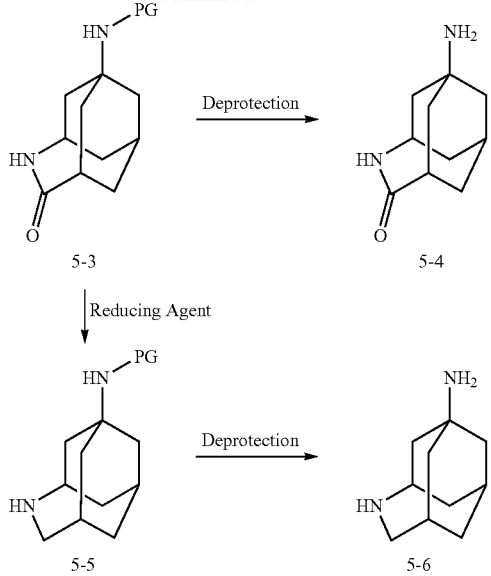

As shown in Scheme 5, ketone 1-1 (PG is an amine protecting group (such as tert-butyloxycarbonyl or Boc; or acetyl)) can be reacted with hydroxylamine resulting in oxime 5-2. Oxime 5-2 can be subjected to Beckman rearrangement conditions, such as strong acid or activation/rearrangement conditions, to provide amide 5-3. Lactam 5-3 can be reduced to amine 5-4 by using a suitable Lewis acid reducing agent such as borane. The protecting group PG of compounds 5-3 and 5-4 can be removed under suitable conditions to afford compounds 5-3 and 5-6.

One of ordinary skill in the art will recognize that some of the compounds of Formula I can exist in different geometrical isomeric forms. In addition, some of the compounds of the present invention possess one or more asymmetric atoms and are thus capable of existing in the form of optical isomers, as well as in the form of racemic or nonracemic mixtures thereof, and in the form of diastereomers and diastereomeric mixtures inter alia. All of these compounds, including cis isomers, trans isomers, diastereomeric mixtures, racemates, nonracemic mixtures of enantiomers, substantially pure, and pure enantiomers, are within the scope of the present invention. In one embodiment, substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereomeric salts using an optically active acid or base or formation of covalent diastereomers.

Examples of appropriate acids include, but are not limited to, tartaric, diacetyltartaric, dibenzoyltartaric, ditoluoyltartaric and camphorsulfonic acid. Mixtures of diastereomers can be separated into their individual diastereomers on the basis of their physical and/or chemical differences by methods known to those skilled in the art, for example, by chromatography or fractional crystallization. The optically active bases or acids are then liberated from the separated diastereomeric salts.

A different process for separation of optical isomers involves the use of chiral chromatography (e.g., chiral HPLC or SFC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivatization, are also useful. The optically active compounds of Formulas I-II can likewise be obtained by utilizing optically active starting materials in chiral syntheses processes under reaction conditions which do not cause racemization.

In addition, one of ordinary skill in the art will recognize that the compounds can be used in different enriched isotopic forms, e.g., enriched in the content of $^2H$, $^3H$, $^{11}C$, $^{13}C$ and/or $^{14}C$. In one particular embodiment, the compounds are deuterated. Such deuterated forms can be made by the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Cum, Pharm. Des., 2000; 6(10)] (2000), 110 pp. CAN 133:68895 AN 2000:473538 CAPLUS; Kabalka, George W.; Varma, Rajender S. The Synthesis of Radiolabeled Compounds via Organometallic Intermediates. Tetrahedron (1989), 45(21), 6601-21, CODEN: TETRAB ISSN: 0040-4020. CAN 112:20527 AN 1990:20527 CAPLUS; and Evans, E. Anthony. Synthesis of radiolabeled compounds, J. Radioanal. Chem. (1981), 64(1-2), 9-32. CODEN: JRACBN ISSN:0022-4081, CAN 95:76229 AN 1981:476229 CAPLUS.

The present invention also relates to useful forms of the compounds as disclosed herein, including free base forms, as well as pharmaceutically acceptable salts or prodrugs of all the compounds of the present invention for which salts or prodrugs can be prepared. Pharmaceutically acceptable salts include those obtained by reacting the main compound, functioning as a base, with an inorganic or organic acid to form a salt, for example, but not limited to, salts of hydrochloric acid, sulfuric acid, phosphoric acid, methanesulfonic acid, camphorsulfonic acid, oxalic acid, maleic acid, succinic acid and citric acid.

Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts are prepared by reacting the compounds of the invention with the appropriate base via a variety of known methods.

The following are further non-limiting examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxyethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

For example, the pharmaceutically acceptable salt can be a hydrochloride, hydroformate, hydrobromide, or maleate.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

One of ordinary skill in the art will also recognize that some of the compounds of Formula I can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

One of ordinary skill in the art will further recognize that compounds of Formula I can exist in different solvate forms. Solvates of the compounds of the invention may also form when solvent molecules are incorporated into the crystalline lattice structure of the compound molecule during the crystallization process. For example, suitable solvates include hydrates, e.g., monohydrates, dihydrates, sesquihydrates, and hemihydrates.

The compounds of the invention can be administered alone or as an active ingredient of a formulation. Thus, the present invention also includes pharmaceutical compositions of one or more compounds of Formula I containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

In view of their high degree of selective M2 channel activity, the compounds of the present invention can be administered to anyone requiring modulation of the M2 channel. Administration may be accomplished according to patient needs, for example, orally, nasally, parenterally (subcutaneously, intravenously, intramuscularly, intrasternally and by infusion) by inhalation, rectally, vaginally, topically and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration, the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

Assays for determining M2 channel activity, and selectivity of M2 channel activity are known within the art. (Schulz et al., *Methods*, 2008, 46, 97-103) See, for example, and Example 17 described below.

In methods using simultaneous administration, the agents can be present in a combined composition or can be administered separately. Similarly, the invention also includes kits containing a composition comprising a compound according to Formula (I) and another composition useful for treating influenza.

The dosages of the compounds of the present invention depend upon a variety of factors including the particular syndrome to be treated, the severity of the symptoms, the route of administration, the frequency of the dosage interval, the particular compound utilized, the efficacy, toxicology profile, pharmacokinetic profile of the compound, the age and medical history of the patient, and the presence of any deleterious side-effects, among other considerations. For example, the dosage can be adjusted depending on whether the compound is administered for the treatment for acute influenza illness or as a prophylaxis to be used for prevention of influenza symptoms. One of ordinary skill in the art of treating such diseases will be able, without undue experimentation and in reliance upon personal knowledge and the disclosure of this Application, to ascertain a therapeutically effective amount of the compounds of the present invention for a given disease.

The compounds of the invention are typically administered at dosage levels and in a mammal customary for M2 channel ligands, such as those known compounds mentioned above. For example, the compounds can be administered, in single or multiple doses, by oral administration at a dosage level of generally 0.001-1000 mg/kg/day, for example, 0.01-300 mg/kg/day, or 0.1-200 mg/kg/day, or 0.5-100 mg/kg/day. Unit dosage forms can contain generally 0.01-1000 mg of active compound, for example, 0.1-100 mg of active compound. For intravenous administration, the compounds can be administered, in single or multiple dosages, at a dosage level of, for example, 0.001-50 mg/kg/day, or 0.001-10 mg/kg/day, or 0.01-1 mg/kg/day. Unit dosage forms can contain, for example, 0.1-10 mg of active compound.

In carrying out the procedures of the present invention, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

In the foregoing and in the following examples, all temperatures are set forth uncorrected in degrees Celsius (° C.); and, unless otherwise indicated, all parts and percentages are by weight.

The entire disclosures of all applications, patents and publications, cited above and below, are hereby incorporated by reference in their entirety.

Abbreviations and Acronyms

When the following abbreviations are used throughout this disclosure, they have the following meaning:

| | |
|---|---|
| Ac | acetyl |
| AIBN | azobisisobutyrylnitrile[2,2'-Azobis(2-methylpropionitrile)] |
| aq | aqueous |
| $BH_3$-$Me_2S$ | borane-dimethylsulfide complex |
| BINAP | 2,2'-bis(diphenylphosphino)-1,1'-binaphthyl |
| Bn | benzyl |
| Boc | tert-butyloxycarbonyl |
| $(Boc)_2O$ | di-tert-butyldicarbonate |
| n-BuLi | n-butyllithium |
| $Bu_3SnH$ | tributyltinhydride |
| t-BuOK | potassium tert-butoxide (potassium 1,1-dimethylethoxide) |
| Cbz | benzyloxycarbonyl |
| ClCOOEt | ethyl chloroformate |
| conc | concentrated |
| d | doublet |
| DAST | diethylaminosulfur trifluoride (N,N-diethylaminosuflur trifluoride) |
| DCM | dichloromethane |
| dd | doublet of doublet |
| ddd | doublet of doublet of doublet |
| Diazald | N-methyl-N-nitroso-p-toluenesulfonamide |
| DEAD | diethylazodiacetate |
| DIBAL | diisobutylaluminum hydride |
| DME | dimethoxyethane |
| DMF | N,N-dimethyl formamide |
| DMSO | dimethylsulfoxide |
| DMSO-$d_6$ | dimethylsulfoxide-$d_6$ |
| E | entgegen |
| eqiv | equivalent |
| ES | electrospray (mass spectrometry) |
| Et | ethyl |
| EtI | iodoethane |
| $Et_2O$ | diethyl ether |
| $Et_3N$ | triethylamine |
| EtOAc | ethyl acetate |
| EtOH | ethanol |
| $Et_3SiH$ | triethylsilane |
| g | gram(s) |
| h | hour(s) |
| HCl | hydrochloric acid |
| $^1$H NMR | proton nuclear magnetic resonance |
| HPLC | high-performance liquid chromatography |
| HPLC ES-MS | high-performance liquid chromatography-electrospray mass spectroscopy |
| HOAc | acetic acid |
| IPA | 2-propanol |
| L | liter |
| LC-MS | liquid chromatography/mass spectroscopy |
| m | multiplet |
| M | molar |
| mCPBA | 3-chloroperbenzoic acid |
| mg | milligram(s) |
| mL | milliliter |
| m/z | mass-to-charge ratio |

| | |
|---|---|
| Me | methyl |
| MeCN | acetonitrile |
| MeI | iodomethane |
| MeOH | methanol |
| MeOD | methanol-$d_4$, $CD_3OD$ |
| MHz | megahertz |
| min | minute(s) |
| mmol | millimole(s) |
| mol | mole |
| MS | mass spectrometry |
| N | normal |
| NaHMDS | sodium bis(trimethylsilyl)amide |
| NBS | N-bromosuccinimide |
| NCS | N-chlorosuccinimide |
| Pd(OAc)$_2$ | palladium acetate |
| Pd/C | palladium on carbon |
| PE | petroleum ether |
| Ph | phenyl |
| Ph$_3$P | triphenylphosphine |
| ppm | parts per million |
| Pr | propyl |
| pTsCl | 4-toluenesulfonyl chloride |
| q | quartet |
| rt | room temperature |
| TBME | tert-butyl methyl ether |
| TEA | triethylamine |
| TEBA | triethylbenzylammonium chloride |
| THF | tetrahydrofuran |
| TosMic | Toluenesulfonylmethyl isocyanide ([1-(isocyanomethylsulfonyl)-4-methylbenzene] |
| $t_R$ | retention time (HPLC) |
| s | singlet |
| t | triplet |
| TFA | trifluoroacetic acid |
| THF | tetrahydrofuran |
| TLC | thin layer chromatography |
| TMS | tetramethylsilane |
| w/w | weight per unit weight |

EXAMPLES

All NMR spectra were recorded at 300 MHz on a Bruker Instruments NMR unless otherwise stated. Coupling constants (J) are in Hertz (Hz) and peaks are listed relative to TMS (δ 0.00 ppm). Microwave reactions were performed using a CEM Discovery™ microwave reactor in 2.5 mL or 5 mL microwave reactor vials. All reactions were performed at 200° C. for 600 s with the fixed hold time ON unless otherwise stated. TLC analysis was performed using Aldrich 254 nm plates (60 Å, 250 vm) and visualized using UV, PMA and KMnO4 stains. Unless otherwise disclosed, the reagents and solvents used in the preparation of the following examples were purchased from commercial sources (Aldrich, VWR, etc.) and used as received.

Analytical HPLC/MS was performed on a 3 mm×50 mm Pursuit 3 Diphenyl column using a gradient of, typically, 5/95 to 100/0 acetonitrile (0.1% formic acid)/water (0.1% formic acid) over 7 min For convenience, compounds are depicted as specific isomers (exo and endo), based on analysis of the physical data obtained for each. While individual pure isomers were obtained in each case, the absolute configuration of stereochemistry of each was not determined by unambiguous means.

Examples 1 and 2

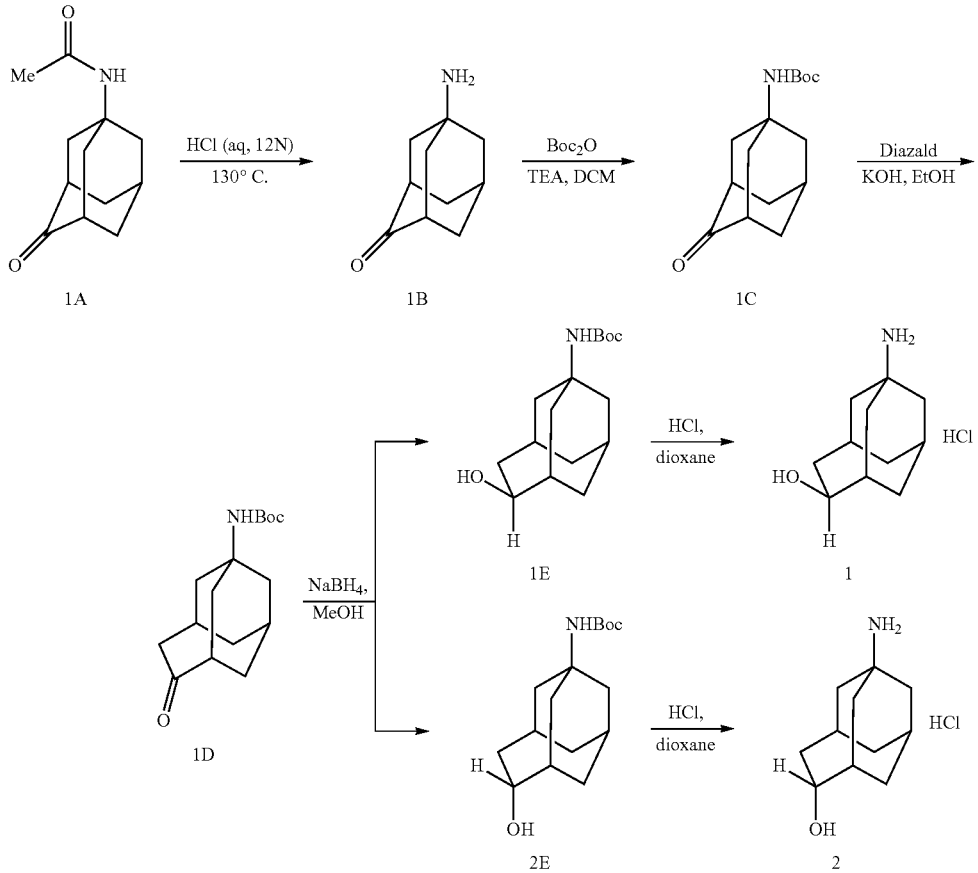

Step 1. Synthesis of 5-aminoadamantan-2-one (1B)

A solution of N-(4-oxoadamantan-1-yl)acetamide (1A) (20 mmol) in 200 mL of concentrated, aqueous HCl was heated in a sealed pressure tube at 130° C. for 20 h. The solvent was removed under reduced pressure to give amine 1B as an HCl salt in 90% yield as an off-white solid. Data: LC/MS (ESR) m/z 166 [M+1]+.

Step 2. Synthesis of tert-Butyl (4-oxoadamantan-1-yl)carbamate (1C)

At 0° C., to a suspension of amine 1B (15 mmol) in DCM (100 mL) was added triethylamine (TEA, 3 mL). A solution of $Boc_2O$ (18 mmol) in DCM (10 mL) was added slowly and the reaction mixture was maintained at rt for 10 h. The reaction was diluted with a saturated, aqueous $NH_4Cl$ solution (50 mL) and the layers were separated. The aqueous layer was extracted with DCM (3×100 mL) and the combined organic layers were dried ($Na_2SO_4$) The solvent was remove under vacuum to provide the carbamate 1C in 90% yield as a solid. The material was used in the next step without further purification. Data: LC/MS (ESR) m/z 266 [M+1]+.

Step 3. Synthesis of tert-butyl (4-oxotricyclo[4.3.1.1³,⁸]undecan-1-yl)carbamate (1D)

A solution of diazomethane (Diazald, 3.97 mmol) was added dropwise to a cold (0° C.) solution of ketone 1C (0.886 mmol) and KOH (40 mmol) in MeOH (10 mL) and water (2 mL) over a period of 3 h. The reaction mixture was allowed to warm to rt and was maintained for 16 h. The resulting white-grey suspension was concentrated and the residue was partitioned between water (10 mL) and DCM (10 mL). The layers were separated and the aqueous layer was extracted with DCM (2×10 mL). The combined organic extracts were dried ($Na_2SO_4$) and the solvent was evaporated to yield ketone 1D in 90% yield. The ketone was used in the next step without further purification. Data: LC/MS (ESR) m/z 280 [M+1]+.

Step 4. Synthesis of exo-tert-butyl (4-hydroxytricyclo[4.3.1.1³,⁸]undecan-1-yl)carbamate (1E) and endo-tert-butyl (4-hydroxytricyclo[4.3.1.1³,⁸]undecan-1-yl)carbamate (2E)

Sodium borohydride (3.88 mmol) was added in one portion to a solution of ketone 1D (1.79 mmol) in MeOH (5 mL) at 0° C. The reaction mixture was allowed to warm to rt and was maintained at rt for 30 min The solution was diluted with a saturated, aqueous $NH_4Cl$ solution (5 mL) and the mixture was extracted with DCM (3×5 mL). The combined organic layers were dried ($Na_2SO_4$) and concentrated. The residue was purified by silica gel chromatography [0/100 to 5/95 MeOH/(50/50 DCM/Hexane)] to give alcohols 1E (250 mg) and 2E (120 mg) as separate compounds. Data: LC/MS (ESR) m/z 282 [M+1]+.

Step 5. Synthesis of exo-1-aminotricyclo[4.3.1.1³,⁸]undecan-4-ol hydrochloride (1) and endo-1-aminotricyclo[4.3.1.1³,⁸]undecan-4-ol hydrochloride (2)

To a solution of carbamate 1E (0.10 mmol) in 2 mL of 1,4-dioxane was added a solution of 4 N HCl in dioxane (1.0 mL) and the mixture was maintained at rt for 16 h. The reaction mixture was concentrated and the residue was dissolved in 2 mL of water and washed with EtOAc (3×5 mL). The aqueous layer was concentrated to give 19 mg of amine 1 as a hydrochloric acid salt.

To a solution of carbamate 2E (0.10 mmol) in 2 mL of 1,4-dioxane was added a solution of 4 N HCl in dioxane (1.0 mL) and the mixture was maintained at rt for 16 h. The reaction mixture was concentrated and the residue was dissolved in 2 mL of water and washed with EtOAc (3×5 mL). The aqueous layer was concentrated to give 17 mg of amine 2 as a hydrochloric acid salt.

Examples 3 and 4

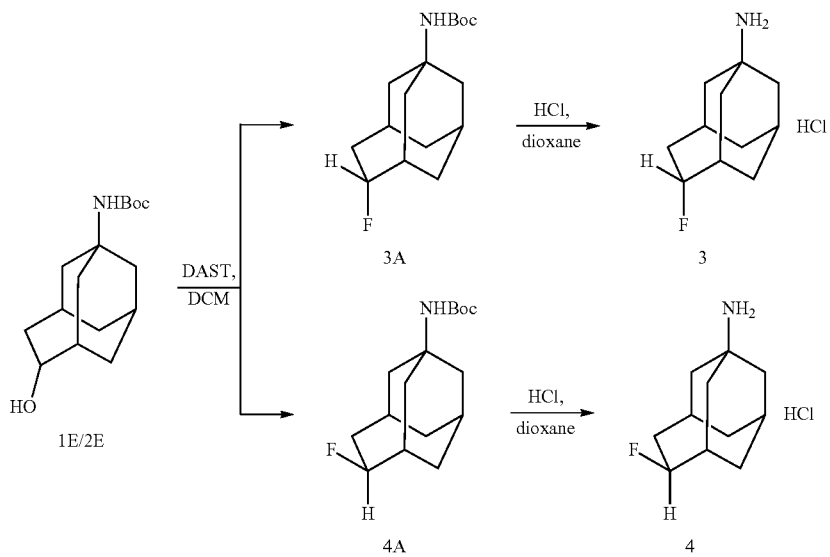

Step 1. Synthesis of endo-tert-butyl (4-fluorotricyclo[4.3.1.1³,⁸]undecan-1-yl)carbamate (3A) and exo-tert-butyl (4-fluorotricyclo[4.3.1.1³,⁸]undecan-1-yl)carbamate (4A)

A solution containing a mixture of epimeric alcohols 1E and 2E (0.711 mmol) in DCM (1 mL) was added dropwise to a solution of (diethylamino)sulfur trifluoride (DAST) (0.854 mmol) in DCM (5 mL) at −78° C. The reaction mixture was allowed to warm to rt and was maintained for 1 h. The reaction mixture was diluted with a saturated, aqueous $NH_4Cl$ solution (2 mL) and the mixture was extracted with DCM (3×5 mL). The combined organic extracts were dried ($Na_2SO_4$) and concentrated. The residue was purified by silica gel chromatography (0/100 to 30/70 EtOAc/hexane) to give fluoride 3A (11%) and fluoride 4A (34%) as separate compounds. A mixture of epimeric fluorides 3A and 4A was also obtained in 30% yield. Data: LC/MS (ESR) adz 284 [M+1]⁺.

Step 2. Synthesis of endo-4-fluorotricyclo[4.3.1.1³,⁸]undecan-1-amine hydrochloride (3) and exo-4-fluorotricyclo[4.3.1.1³,⁸]undecan-1-amine hydrochloride (4)

To a solution of carbamate 3A (0.10 mmol) in 1,4-dioxane (2 mL) was added a solution of 4 N HCl in dioxane (1.0 mL) and the mixture was maintained at rt for 16 h. The reaction mixture was concentrated and the residue was dissolved in water (2 mL). The aqueous layer was washed with EtOAc (3×5 mL) and concentrated to provide 19 mg of amine (3) as a hydrochloric acid salt.

To a solution of carbamate 4A (0.10 mmol) in 1,4-dioxane (2 mL) was added a solution of 4 N HCl in dioxane (1.0 mL) and the mixture was maintained at rt for 16 h. The reaction mixture was concentrated and the residue was dissolved in water (2 mL). The aqueous layer was washed with EtOAc (3×5 mL) and concentrated to provide 21 mg of amine (4) as a hydrochloric acid salt.

Example 5

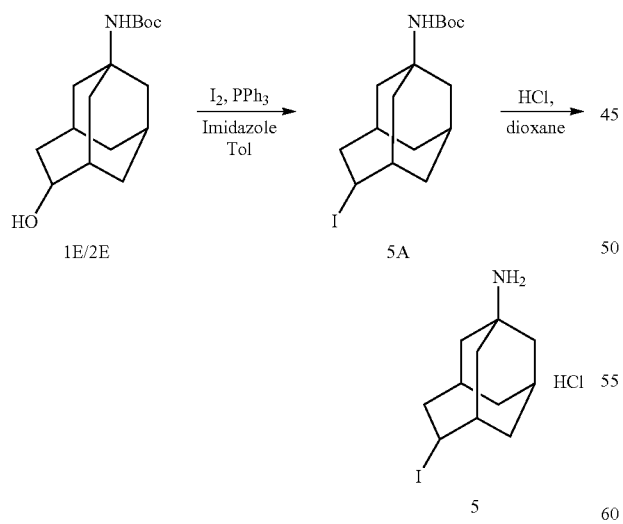

Step 1. Synthesis of tert-butyl (4-iodotricyclo[4.3.1.1³,⁸]undecan-1-yl)carbamate (5A)

A mixture of epimeric alcohols 1E and 2E (0.18 mmol) was added at one portion to a stirred suspension of $I_2$ (2.49 mmol), $PPh_3$ (0.267 mmol), and imidazole (0.37 mmol) in toluene (5 mL). The reaction mixture was heated at 80° C. for 2 h and was concentrated. The residue was purified by silica gel chromatography (0/100 to 6/94 EtOAc/hexane) to provide the epimeric mixture of iodides 5A in 50% yield. Data: LC/MS (ESR) m/z 392 [M+1]⁺.

Step 2. Synthesis of 4-iodotricyclo[4.3.1.1³,⁸]undecan-1-amine hydrochloride (5)

To a solution of carbamate 5A (0.10 mmol) in 1,4-dioxane (2 mL) was added a solution of 4 N HCl in dioxane (1.0 mL) and the mixture was maintained at rt for 16 h. The reaction mixture was concentrated and the residue was dissolved in water (2 mL). The aqueous layer was washed with EtOAc (3×5 mL) and concentrated to provide amine (5) in 64% yield as a hydrochloric acid salt. Data: LC/MS (ESR) m/z 292 [M+1]⁺.

Example 6

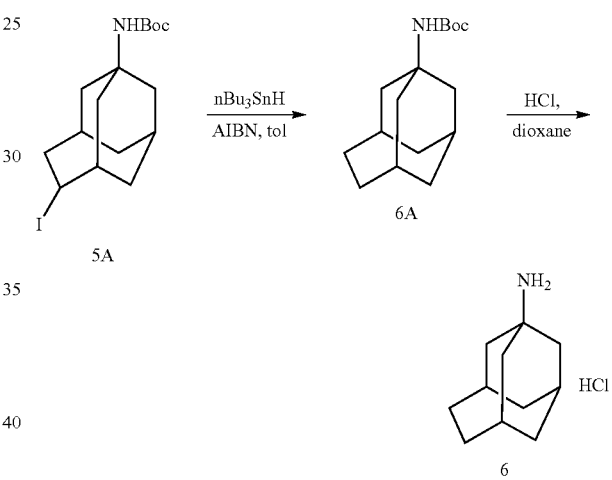

Step 1. Synthesis of tert-butyl tricyclo[4.3.1.1³,⁸]undecan-1-ylcarbamate (6A)

The mixture of iodide 5A (0.18 mmol), AIBN (0.054 mmol), and $Bu_3SnH$ (0.54 mmol) was diluted with toluene (10 mL) and the reaction mixture was heated at 90° C. for 2 h. The reaction mixture was concentrated and the residue was purified by silica gel chromatography (10/90 EtOAc/Hexane) to provide the reduction product 6A in 73% yield. Data: LC/MS (ESR) m/z 266 [M+1]⁺.

Step 2. Synthesis of tricyclo[4.3.1.1³,⁸]undecan-1-amine hydrochloride (6)

To a solution of carbamate 6A (0.13 mmol) in 1,4-dioxane (2 mL) was added a solution of 4 N HCl in dioxane (1.0 mL) and the mixture was maintained at rt for 16 h. The reaction mixture was concentrated and the residue was dissolved in water (2 mL). The aqueous layer was washed with EtOAc (3×5 mL) and concentrated to provide amine 5 in 95% yield as a hydrochloric acid salt.

Examples 8 and 9

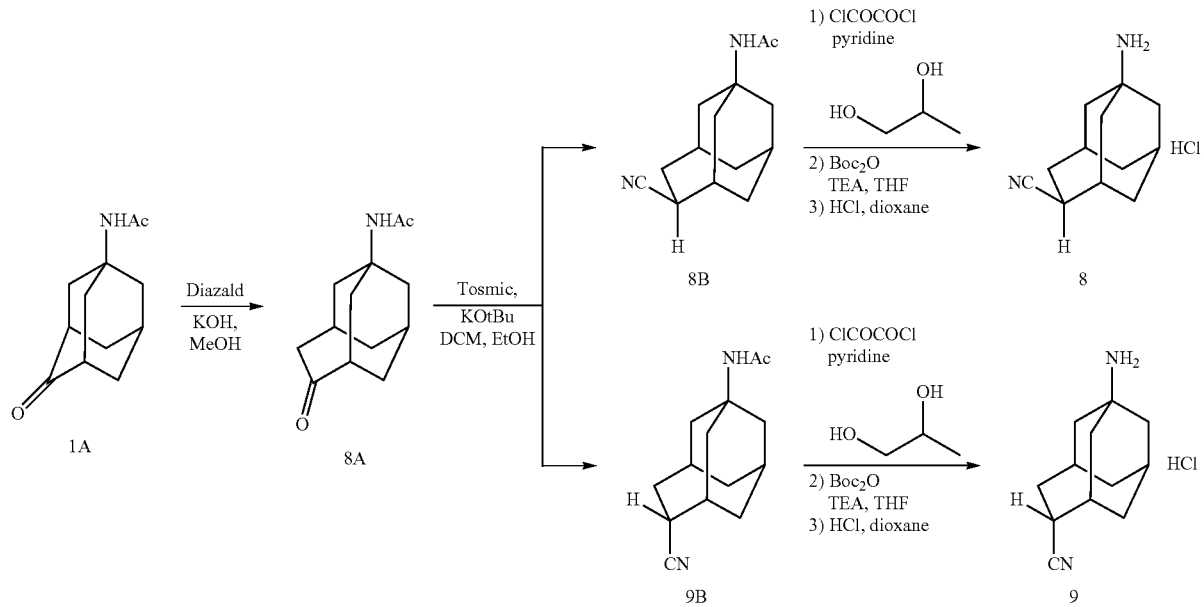

Step 1. Synthesis of N-(4-oxotricyclo[4.3.1.1$^{3,8}$]undecan-1-yl)acetamide (8A)

A solution of diazomethane (Diazald, 2.70 g) in MeOH (15 mL) was added dropwise to a mixture of ketone 1A (997 mg) and KOH (3.81 g) in MeOH (10 mL) and water (1.8 mL) at 0° C. over a period of 1.5 h. The reaction mixture was allowed to warm to rt and was maintained for 16 h. The resulting suspension was concentrated and was diluted with water (50 mL). The resulting aqueous suspension was extracted with ether (1×), then with DCM (2×), and the combined organic layers were dried (Na$_2$SO$_4$) and concentrated. The residue was purified by silica gel chromatography (0/100 to 10/90 MeOH/EtOAc) to provide 964 mg of ketone 8A as a white solid. Data: LC/MS (ESR) m/z 222 [M+1]$^+$, 244 [M+Na]$^+$.

Step 2. Synthesis of exo-N-(4-cyanotricyclo[4.3.1.1$^{3,8}$]undecan-1-yl)acetamide (8B) and endo-N-(4-cyanotricyclo[4.3.1.1$^{3,8}$]undecan-1-yl)acetamide (9B)

Solid t-BuOK (346 mg) was added as 6 portions to a solution of ketone 8A (105 mg) and TosMIC (265 mg) in a mixture of DME (4.0 mL) and absolute EtOH (0.15 mL) while keeping the temperature between 5 and 10° C. The reaction mixture was allowed to warm to rt and was maintained for 30 min The reaction mixture was then heated at 35-40° C. for 30 min and was then allowed to cool to rt. The precipitate (TosK) was removed by filtration and the filter cake was washed with DME. The combined organic layers were concentrated and the residue was purified by column chromatography (0/100 to 10/90 MeOH/EtOAc) to provide nitrile 8B (44.3 mg) and nitrile 9B (35.6 mg) as separate compounds. Data: LC/MS (ESR) m/z 233 [M+1]$^+$.

Step 3. Synthesis of exo-Faminotricyclo[4.3.1.1$^{3,8}$]undecane-4-carbonitrile hydrochloride (8) and endo-1-aminotricyclo[4.3.1.1$^{3,8}$]undecane-4-carbonitrile hydrochloride (9)

A 2.0 M solution of oxalyl chloride in DCM (0.10 mL) was added dropwise to a solution of amide 8B (42.0 mg) in dry THF (3 mL) and pyridine (0.02 mL) at 0° C. The reaction mixture was maintained at 0° C. for 45 min when 1,2-propanediol (0.03 mL) was added in one portion and the reaction was allowed to warm to rt. The reaction mixture was diluted with EtOH (4 mL) and was concentrated. The crude oil was partitioned between 1 M aqueous HCl and TBME (10 mL) and the layers were separated. The organic phase was extracted with 1.0 M aqueous HCl solution (1×) and the pH of the combined aqueous layers was adjusted to pH 11 with 4 N aqueous NaOH. The aqueous layer was then extracted EtOAc (2×) and the combined organic layers were dried (Na$_2$SO$_4$), and concentrated to provide the crude amine.

Boc-anhydride (69.9 mg) and TEA (0.3 mL) was added sequentially to a solution of the crude amine in THF (3 mL) and the reaction mixture was maintained at rt for 2 h. The reaction mixture was diluted with NaHCO$_3$ solution and the aqueous layer was extracted with EtOAc (2×). The combined organic layers were dried (Na$_2$SO$_4$) and concentrated. The residue was purified by silica gel chromatography (0/100 to 30/70 EtOAc/hexane) to provide 30.1 mg of the pure carbamate.

The carbamate (30.1 mg) was diluted with a solution of 4 N HCl in dioxane (1.5 mL) and the reaction mixture was maintained at rt for 2 h. The reaction mixture was concentrated and the residue was triturated with ether (3×) and dried to provide 21.6 mg of amine 8 as a white solid.

Nitrile 9 was prepared using the reaction conditions that were used to prepare nitrile 8.

Examples 10 and 11

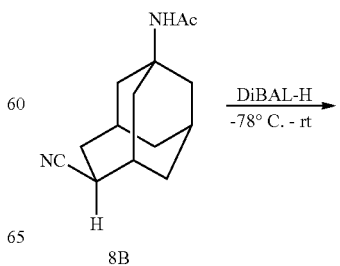

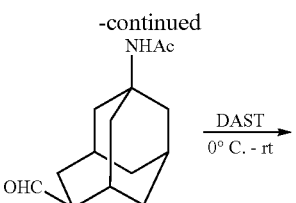

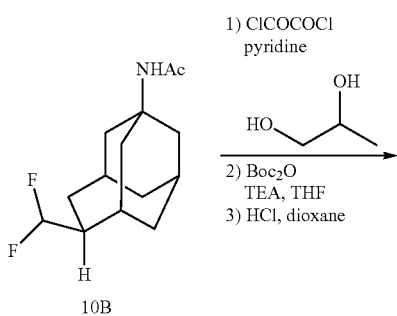

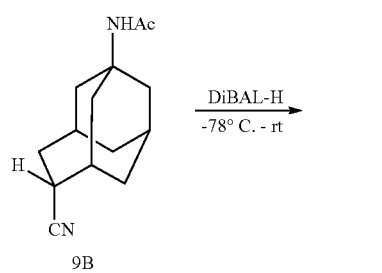

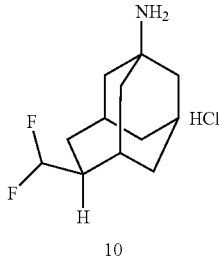

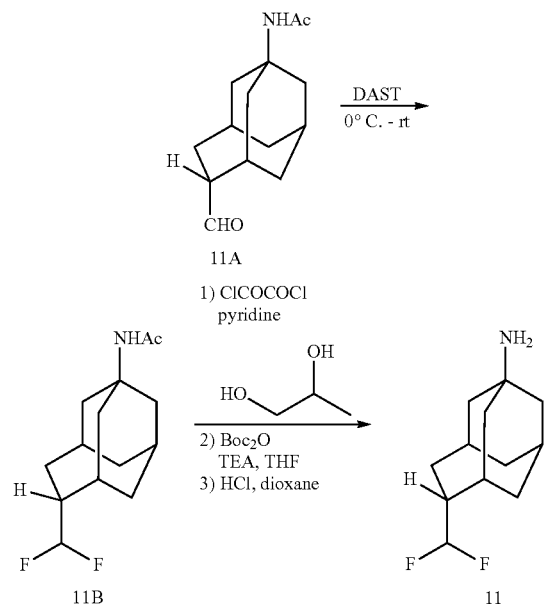

Step 1. Synthesis of exo-N-(4-formyltricyclo [4.3.1.1$^{3,8}$]undecan-1-yl)acetamide (10A) and endo-N-(4-formyltricyclo[4.3.1.1$^{3,8}$]undecan-1-yl)acetamide (11A)

A 1.0 M solution of DIBAL-H in hexane (1 8 mmol) was added dropwise to a solution of nitrile 8B (160 mg) in THF (4.0 mL) at −78° C. The reaction mixture was allowed to slowly warm to rt and maintained at rt for 3 h. The reaction was carefully quenched with a 1 M aqueous solution of HCl. The reaction mixture was extracted with EtOAc (2×) and the combined organic layers were dried (Na$_2$SO$_4$), and concentrated. The residue was purified by silica gel chromatography (0/100 to 10/90 MeOH/EtOAc) to provide 50.6 mg of aldehyde 10A. Data: LC/MS (ESR) m/z 236 [M+1]$^+$.

Aldehyde 11A was prepared from nitrile 9B using the reaction conditions that were used to prepare aldehyde 10A. Data: LC/MS (ESR) m/z 236 [M+1]$^+$.

Step 2. Synthesis of exo-N-(4-(difluoromethyl)tricyclo[4.3.1.1$^{3,8}$]undecan-1-yl)acetamide (10B) and endo-N-(4-(difluoromethyl)tricyclo [4.3.1.1$^{3,8}$]undecan-1-yl)acetamide (11B)

DAST (0.15 mL) was added dropwise over a period of 10 min to a solution of aldehyde 10A (60.2 mg) in DCM (5 mL) at −78° C. The reaction mixture was maintained at −78° C. for 10 min and then was allowed to slowly warm to rt. After 1 h at rt, the reaction was carefully diluted with water and was extracted with EtOAc (2×). The combined organic layers were dried (Na$_2$SO$_4$), and concentrated. The residue was purified by silica gel chromatography (0/100 to 5/95 MeOH/EtOAc) to provide 48.0 mg of difluoromethyl analog 10B. Data: LC/MS (ESR) m/z 258 [M+1]$^+$.

Difluoromethyl analog 11B was prepared from aldehyde 11A using the reaction conditions that were used to prepare the difluoromethyl analog 10B. Data: LC/MS (ESR) m/z 258 [M+1]$^+$.

Step 3. Synthesis of exo-4-(difluoromethyl)tricyclo [4.3.1.1$^{3,8}$]undecan-1-amine hydrochloride (10) and endo-4-(difluoromethyl)tricyclo[4.3.1.1$^{3,8}$]undecan-1-amine hydrochloride (11)

A 2.0 M solution of oxalyl chloride in DCM (0.10 mL) was added dropwise to a solution of amide 10B (40.0 mg) in dry THF (5 mL) and pyridine (0.02 mL) at 0° C. The reaction mixture was maintained at 0° C. for 45 min when 1,2-propanediol (0.04 mL) was added in one portion and the reaction was allowed to warm to rt. The reaction mixture was diluted with EtOH (4 mL) and was concentrated. The crude oil was partitioned between 1 M aqueous HCl and TBME (10 mL) and the layers were separated. The organic phase was extracted with 1.0 M aqueous HCl solution (1×) and the pH of the combined aqueous layers was adjusted to pH 11 with 4 N aqueous NaOH. The aqueous layer was then extracted EtOAc (2×) and the combined organic layers were dried (Na$_2$SO$_4$), and concentrated to provide the crude amine.

Boc-anhydride (57.8 mg) and TEA (0.3 mL) was added sequentially to a solution of the crude amine in THF (3 mL) and the reaction mixture was maintained at rt for 2 h. The reaction mixture was diluted with NaHCO$_3$ solution and the aqueous layer was extracted with EtOAc (2×). The combined organic layers were dried (Na$_2$SO$_4$) and concentrated. The residue was purified by silica gel chromatography (0/100 to 20/80 EtOAc/hexane) to provide 24.0 mg of the pure carbamate.

The pure carbamate (24.0 mg) was diluted with a solution of 4 N HCl in dioxane (1.5 mL) and the reaction mixture was maintained at rt for 2 h. The reaction mixture was concentrated and the residue was triturated with ether (3×) and dried to provide 20.6 mg of amine 10 as a white solid.

Amine 11 was prepared from amide 11B using the reaction conditions that were used to prepare amine 10.

Example 12

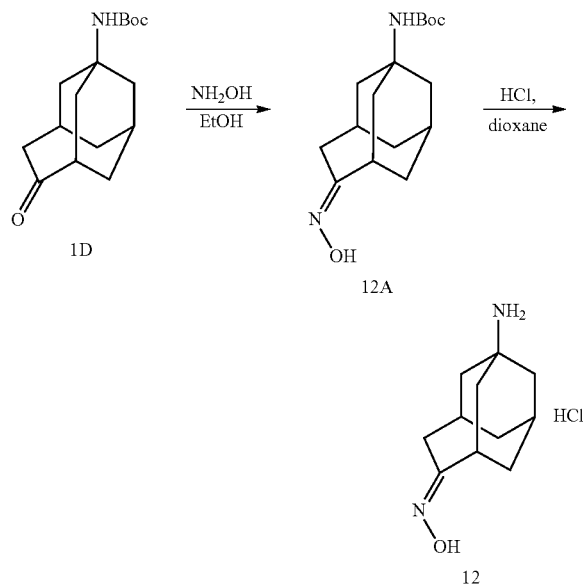

Step 1. Synthesis of tert-butyl (4-(hydroxyimino) tricyclo[4.3.1.1³,⁸]undecan-1-yl)carbamate (12A)

The mixture of ketone 1D (10 mmol), NH₂OH—HCl (5 mmol), and NaOH (5 mmol) was diluted with EtOH (5 mL) and H₂O (1 mL) and the reaction mixture was heated at 80° C. for 16 h. Upon cooling, the reaction mixture was extracted with DCM (10 mL×3) and the combined organic layers were dried (Na₂SO₄) and concentrated to provide oxime 12A in 90% yield as a solid. The material was used in the next step without further purification. Data: LC/MS (ESR) m/z 295 [M+1]⁺.

Step 2. Synthesis of 1-aminotricyclo[4.3.1.1³,⁸]undecan-4-one oxime hydrochloride (12)

A solution of oxime 12A (0.17 mmol) in 1,4-dioxane (2.0 mL) was diluted with a solution of 4 N HCl in dioxane (1.0 mL) and the reaction mixture was maintained at rt for 16 h. The reaction mixture was concentrated and dried to provide amine 10 in 88% yield as a hydrochloric acid salt.

Example 13

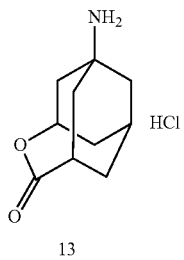

Step 1. Synthesis of tert-butyl (5-oxo-4-oxatricyclo [4.3.1.1³,⁸]undecan-1-yl]carbamate (13A)

Solid NaHCO₃ (0.3 mol) and mCPBA (0.3 mmol, 77% purity) were added to a solution of ketone 1C (0.19 mmol) in DCM (5 mL) t 0° C. The reaction mixture was allowed to warm to rt and was maintained for 1 h. The reaction mixture was diluted with a saturated, aqueous solution of sodium bisulfate (10 mL) and was extracted with DCM (3×5 mL). The combined organic layers were dried (Na₂SO₄) and concentrated. The residue was purified by silica gel chromatography (10/90 to 30/70 EtOAC/hexane) to provide lactone 13A in 85% yield. Data: LC/MS (ESR) m/z 282 [M+1]⁺.

Step 2. Synthesis of 1-amino-4-oxatricyclo[4.3.1. 1³,⁸]undecan-5-one hydrochloride (13)

To a solution of lactone 13A (0.17 mmol) in 1,4-dioxane (2 mL) was added a solution of 4 N HCl in dioxane (1.0 mL) and the mixture was maintained at rt for 16 h. The reaction mixture was concentrated and the residue was dissolved in water (2 mL). The aqueous layer was washed with EtOAc (3×5 mL) and concentrated to provide amine 13 in 95% yield as a hydrochloric acid salt.

Example 14

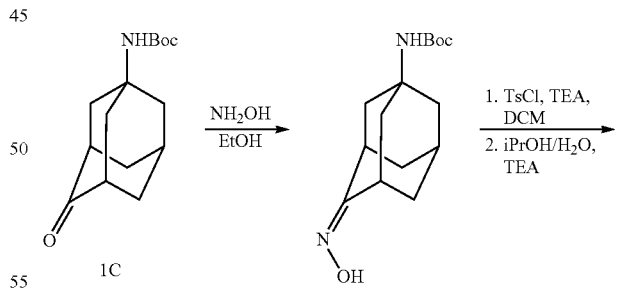

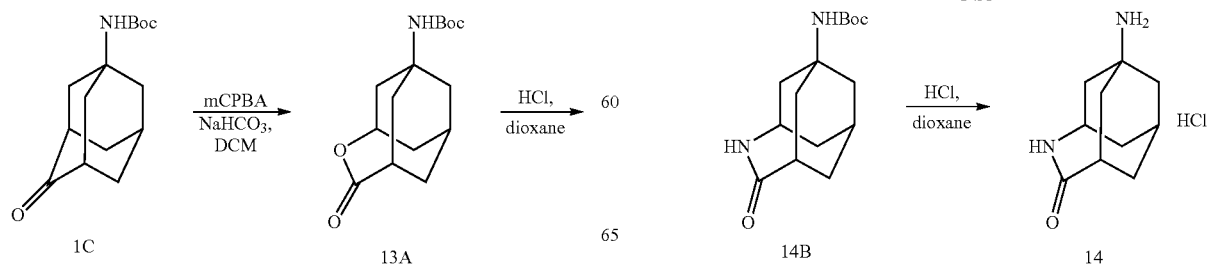

Step 1. Synthesis of tert-butyl [4-(hydroxyimino)adamantan-1-yl]carbamate (14A)

The mixture of ketone 1C (3 0 mmol), $NH_2OH \cdot HCl$ (5 mmol), and NaOH (5 mmol) was diluted with EtOH (5 mL) and $H_2O$ (1 mL) and the reaction mixture was heated at 80° C. for 16 h. Upon cooling, the reaction mixture was extracted with DCM (10 mL×3) and the combined organic layers were dried ($Na_2SO_4$) and concentrated to provide oxime 14A in 90% yield as a solid. The material was used in the next step without further purification. Data: LC/MS (ESR) m/z 281 [M+1]$^+$.

Step 2. Synthesis of tert-butyl (5-oxo-4-azatricyclo [4.3.1.1$^{3,8}$]undecan-1-yl)carbamate (14B)

Solid p-TsCl (4 mmol) was added to a solution of oxime 14A (2.7 mmol) in TEA (2 mL) and DCM (20 mL) at rt and the reaction mixture was maintained for 20 h. The reaction mixture was concentrated and the residue was dissolved in IPA (8 mL), $H_2O$ (2 mL), and TEA (2 mL). The reaction mixture was heated at 90° C. for 3 h and was allowed to cool to rt. The reaction mixture was concentrated to a volume of ~3 mL and the residue was extracted with DCM (3×10 mL). The combined organic layers were dried ($Na_2SO_4$) and concentrated. The residue was purified by silica gel chromatography (0/100 to 10/90 MeOH/DCM) to provide lactam 14B in 65% yield. Data: LC/MS (ESR) m/z 281 [M+1]$^+$.

Step 3. Synthesis of 1-amino-4-azatricyclo[4.3.1.1$^{3,8}$]undecan-5-one hydrochloride (14)

To a solution of lactam 14B (0.18 mmol) in 1,4-dioxane (2 mL) was added a solution of 4 N HCl in dioxane (1.0 mL) and the mixture was maintained at rt for 16 h. The reaction mixture was concentrated and the residue was dissolved in water (2 mL). The aqueous layer was washed with EtOAc (3×5 mL) and concentrated to provide amine 14 in 88% yield as a hydrochloric acid salt.

Example 15

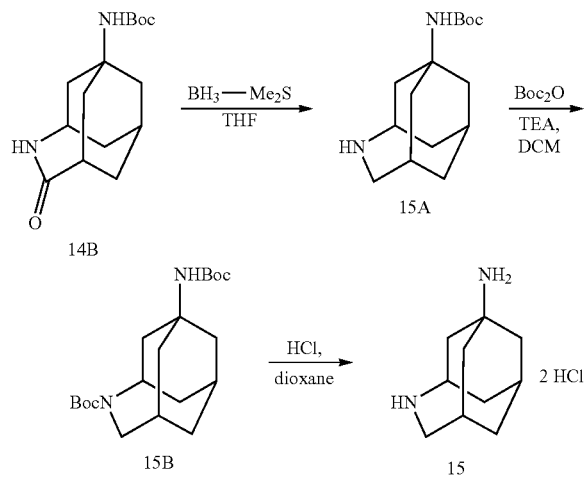

Step 1. Synthesis of tert-butyl 4-azatricyclo[4.3.1.1$^{3,8}$]undecan-1-ylcarbamate (15A)

A 1.0 M solution of $BH_3$-$Me_2S$ in THF (1 5 mmol) was added dropwise to a solution of amide 14B (0.125 mmol) in THF (5 mL). The reaction mixture was heated at reflux for 2 h and was allowed to cool to rt. MeOH (2 mL) was cautiously added and the reaction mixture was concentrated. The residue was triturated with DCM (3×10 mL) and the combined organic layers were dried ($Na_2SO_4$) and concentrated to provide amine 15A. The amine was used in the next step without further purification. Data: LC/MS (ESR) m/z 167 [M+1]$^+$.

Step 2. Synthesis of tert-butyl 1-((tert-butoxycarbonylamino)-4-azatricyclo[4.3.1.1$^{3,8}$]undecane-4-carboxylate (15B)

$Boc_2O$ (0.5 mmol) and triethylamine (0.5 mL) were added to a solution of amine 15A in DCM (2 mL) at 0° C. The reaction mixture was allowed to warm to rt and was maintained for 2 h. The reaction mixture was diluted with a saturated, aqueous $NH_4Cl$ solution (1 mL) and the mixture was extracted with DCM (3×5 mL). The combined DCM layers were dried ($Na_2SO_4$) and concentrated. The residue was purified by silica gel chromatography (10/90 to 30/70 EtOAc/Hexane) to provide carbamate 15B in 65% yield. Data: LC/MS (ESR) m/z 267 [M+1]$^+$.

Step 3. Synthesis of 4-azatricyclo[4.3.1.1$^{3,8}$]undecan-1-amine dihydrochloride (15)

To a solution of carbamate 15B (0 1 mmol) in 1,4-dioxane (1 mL) was added a solution of 4 N HCl in dioxane (0.5 mL) and the mixture was maintained at rt for 16 h. The reaction mixture was concentrated and the residue was dissolved in water (2 mL). The aqueous layer was washed with EtOAc (3×5 mL) and concentrated to provide amine 15 in 80% yield as a hydrochloric acid salt.

Example 16

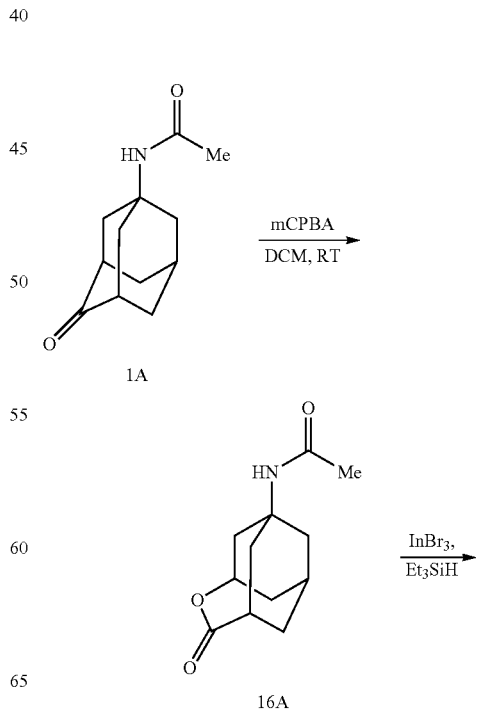

-continued

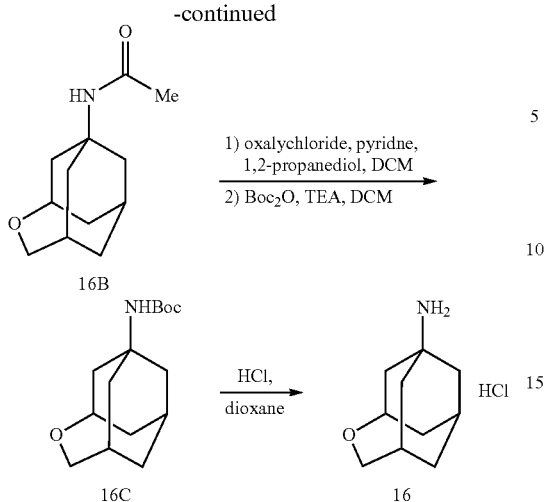

Step 1. Synthesis of N-(5-oxo-4-oxatricyclo[4.3.1.1³,⁸]undecan-1-yl)acetamide (16A)

Solid NaHCO₃ (1.2 mol) and mCPBA (1 2 mmol, 77% purity) were added to a solution of ketone 1A (0.6 mmol) in DCM (5 mL) at 0° C. The reaction mixture was allowed to warm to rt and was maintained for 1 h. The reaction mixture was diluted with a saturated, aqueous solution of sodium bisulfate (10 mL) and was extracted with DCM (3×10 mL). The combined organic layers were dried (Na₂SO₄) and concentrated. The residue was purified by silica gel chromatography (10/90 to 30/70 EtOAc/hexane) to provide lactone 16A in 90% yield. Data: LC/MS (ESR) m/z 224 [M+1]⁺.

Step 2. Synthesis of N-(4-oxatricyclo[4.3.1.1³,⁸]undecan-1-yl)acetamide (16B)

InBr₃ (0.056 mmol) and Et₃SiH (12.6 mmol) were successively added to a solution of lactone 16A (0.54 mmol) in CHCl₃ (5 mL) and the reaction mixture was heated at 60° C. for 1 h. The reaction mixture was allowed to cool to rt, was diluted with H₂O (10 mL), and the layers were separated. The aqueous layer was extracted with DCM (3×10 mL) and the combined organic layers were dried (Na₂SO₄) and concentrated. The residue was purified by silica gel chromatography (10/90 to 30/70 EtOAc/hexane) to provide ether 16B in 70% yield. Data: LC/MS (ESR) m/z 210 [M+1]⁺.

Step 3. Synthesis of tert-butyl 4-oxatricyclo[4.3.1.1³,⁸]undecan-1-ylcarbamate (16C)

A 2.0 M solution of oxalyl chloride in DCM (0.30 mmol) was added dropwise to a solution of amide 16B (0.29 mmol) in dry THF (2 mL) and pyridine (0.3 mL) at 0° C. The reaction mixture was maintained at 0° C. for 30 min when 1,2-propanediol (0.5 mL) was added in one portion and the reaction was allowed to warm to rt. The reaction mixture was diluted with EtOH (5 mL) and was concentrated. The crude oil was partitioned between 1 M aqueous HCl (2 mL) and TBME (5 mL) and the layers were separated. The organic phase was extracted with 1.0 M aqueous HCl solution (2×5 mL) and the pH of the combined aqueous layers was adjusted to pH 11 with 4 N aqueous NaOH. The aqueous layer was then extracted with DCM (3×5 mL) and the combined organic layers were dried (Na₂SO₄), and concentrated to provide the crude amine. Data: LC/MS (ESR) m/z 167 [M+1]⁺.

Boc-anhydride (0.5 mmol) and TEA (0.5 mL) was added sequentially to a solution of the crude amine in DCM (2 mL) and the reaction mixture was maintained at rt for 2 h. The reaction mixture was diluted with a saturated, aqueous solution of NH₄Cl (1 mL) and the aqueous layer was extracted with DCM (3×5 mL). The combined organic layers were dried (Na₂SO₄) and concentrated. The residue was purified by silica gel chromatography (10/90 to 30/70 EtOAc/hexane) to provide the pure carbamate 16C in 26% yield. Data: LC/MS (ESR) m/z 267 [M+1]⁺.

Step 4. Synthesis of 4-oxatricyclo[4.3.1.1³,⁸]undecan-1-amine hydrochloride (16)

The carbamate 16C (0.1 mmol) in 1,4-dioxane (1 mL) was diluted with a solution of 4 N HCl in dioxane (0.5 mL) and the reaction mixture was maintained at rt for 2 h. The reaction mixture was concentrated and the residue was dissolved in water (2 mL). The aqueous layer was washed with EtOAc (3×5 mL) and concentrated to provide amine 16 in 80% yield as a hydrochloric acid salt.

Example 17

Cell-free Electrophysiology of M2 Proton Channels

The drug sensitivity of A/M2 proteins (wild type or S31N mutant) was measured using cell-free electrophysiology on solid supported membranes (SSM) (Schulz et al., Methods, 2008, 46, 97-103). For the SSM-based measurements cell membranes expressing the target protein are adsorbed to an SSM-coated gold sensor and the protein activity is evoked by substrate, or ligand concentration jumps, as appropriate. The resulting protein-dependent charge translocation is measured as a transient electrical current.

SSM-based Biosensors and Measurements

The biosensors were prepared with single-gold-electrode sensors from IonGate Biosciences (Germany) as described by the manufacturer. Briefly, the SSM was built on the gold electrode by applying first an alkane-thiol monolayer followed by a phospholipid monolayer on top of it. Subsequently, the SSM-coated sensors were covered with 100 µl of the ice cold M2 sensor preparation buffer (30 mM MES/KOH, pH 5.8, 140 KCl, 4 mM MgCl₂, 0.2 mM DTT) and incubated at 4° C. for 15 minutes. An aliquot of CHO membranes expressing M2 protein was rapidly thawed, diluted with the sensor preparation buffer to a final protein concentration of 0.5-1 µg/µL, and sonicated with a microsonicator by applying 5 bursts with an amplitude of 30% (ultrasonic processor UP 50 H with a MS 1 tip, Dr. Hielscher, Germany). 5-10 µg total protein of the sonicated membranes were loaded per each sensor, centrifuged for 30 minutes at 3,000 rpm and 4° C., and incubated for 24 hours at 4° C. The membrane-loaded biosensors were integrated into the fluidic system of the SURFE²R device (Surface Electrogenic Event Reader, IonGate Biosciences, Germany) and the A/M2 was activated through pH jumps by exchanging a "non-activating" solution (30 mM MOPS/KOH, pH 7.0, 140 KCl, 4 mM MgCl₂) for an "activating" solution (30 mM MES/KOH, pH 6.0, 140 KCl, 4 mM MgCl₂). For the inhibition experiments, the compounds to be tested as inhibitors were supplied at the same concentration to both solutions. Responses in the presence of the compounds of Formula (I) were normalized to the currents evoked by the application of the activating (pH 6.0) solution without inhibitor (Io) and are calculated as % inhibition=100×(1−I/Io).

Representative compounds of Formula (I) were tested using the above protocol with results summarized in Table 2. The resulting inhibition is indicated as falling into one of three ranges: 51-95% (A), 11-50% (B), and 1-10% (C):

TABLE 2

| Example No | IonGate S31 (% Inhibition Range at 25 μM)[1] |
|---|---|
| 1 | B |
| 2 | B |
| 3 | A |
| 4 | A |
| 5 | B |
| 8 | A |
| 9 | A |
| 10 | B |
| 11 | A |
| 12 | C |
| 13 | C |
| 14 | C |
| 15 | B |
| 16 | B |

[1]Range: 51-95% (A), 11-50% (B), and 1-10% (C)

We claim:

1. A compound of Formula I:

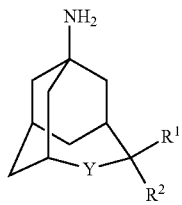

(I)

wherein
Y is selected from $CH_2$, C(=O), C(=NOR$^7$), and O;
$R^1$ and $R^2$ are each independently selected from
H, halo, cyano, OR$^7$, C(O)R$^{10}$, $C_1$-$C_6$ alkyl, and $C_1$-$C_6$ halogenated alkyl, provided that when Y is $CH_2$, at least one of $R^1$ or $R^2$ is other than H;
or
$R^1$ and $R^2$ together form a double bond functional group selected from oxo (=O) and oximino (=N—OR$^7$);
$R^7$ is selected from
H, $C_1$-$C_6$ alkyl, $C_1$-$C_6$ halogenated alkyl, $C_3$-$C_6$ alkenyl, $C_3$-$C_6$ alkynyl, $C_3$-$C_8$ cycloalkyl, $C_5$-$C_8$ cycloalkenyl, and C(O)R$^{10}$;
$R^{10}$ is selected from
H, $C_1$-$C_6$ alkyl, $C_1$-$C_6$ halogenated alkyl, $C_3$-$C_6$ alkenyl, $C_3$-$C_6$ alkynyl, $C_3$-$C_8$ cycloalkyl, and $C_5$-$C_8$ cycloalkenyl;
or a pharmaceutically acceptable salt thereof.

2. A compound according to claim 1 wherein Y is O.

3. A compound according to claim 2 wherein Y is O, and $R^1$ and $R^2$ are both H.

4. A compound according to claim 1 wherein Y is $CH_2$.

5. A compound according to claim 4 wherein $R^1$ and $R^2$ are independently selected from H, halo, $C_1$-$C_6$ alkyl, and OR$^7$; and $R^7$ is H.

6. A compound according to claim 4 wherein $R^1$ and $R^2$ together form a double bond functional group selected from oxo (=O), and oximino (=N—OR$^7$).

7. A compound selected from
exo-1-aminotricyclo[4.3.1.1$^{3,8}$]undecan-4-ol hydrochloride,
endo-1-aminotricyclo[4.3.1.1$^{3,8}$]undecan-4-ol hydrochloride,
endo-4-fluorotricyclo[4.3.1.1$^{3,8}$]undecan-1-amine hydrochloride,
exo-4-fluorotricyclo[4.3.1.1$^{3,8}$]undecan-1-amine hydrochloride,
4-fluorotricyclo[4.3.1.1$^{3,8}$]undecan-1-amine hydrochloride,
4-iodotricyclo[4.3.1.1$^{3,8}$]undecan-1-amine hydrochloride,
exo-1-aminotricyclo[4.3.1.1$^{3,8}$]undecane-4-carbonitrile hydrochloride,
endo-1-aminotricyclo[4.3.1.1$^{3,8}$]undecane-4-carbonitrile hydrochloride,
exo-4-(difluoromethyl)tricyclo[4.3.1.1$^{3,8}$]undecan-1-amine hydrochloride,
endo-4-(difluoromethyl)tricyclo[4.3.1.1$^{3,8}$]undecan-1-amine hydrochloride,
1-aminotricyclo[4.3.1.1$^{3,8}$]undecan-4-one oxime hydrochloride,
4-oxatricyclo[4.3.1.1$^{3,8}$]undecan-1-amine hydrochloride,
and the pharmaceutically acceptable salts thereof.

8. A method for treating an Influenza A infection in a mammal comprising administering to a mammal in need thereof an effective amount of the compound of claim 1.

9. A method for treating an Influenza A infection in a mammal by inhibition of a viroporin membrane protein of the Influenza A virus, comprising administering to a mammal in need thereof an effective amount of the compound of claim 1.

10. The method according to claim 9 wherein the site of inhibition of the viroporin membrane protein is selected from the M2 proton channel of Influenza A virus.

11. The method according to claim 8 wherein the compound is administered in combination with a therapeutically effective amount of one or more agents active against Influenza A.

12. The method according to claim 11 wherein said active agent is selected from Tamiflu® (oseltamivir), Relenza®, and peramivir.

13. A pharmaceutical composition comprising the compound of claim 1 and a pharmaceutically acceptable carrier diluent or excipient.

14. A method of treating an Influenza A infection in a mammal comprising administering to a mammal in need thereof, a therapeutically effective amount of the compound of claim 1 in combination with immunizations or vaccines that are effective in preventing or lessening the symptoms of Influenza A.

* * * * *